United States Patent
Gupta et al.

(10) Patent No.: US 9,650,641 B2
(45) Date of Patent: May 16, 2017

(54) ZEA MAYS PROMOTER FROM CHLOROPHYLL A/B BINDING PROTEIN GENE AND USES THEREOF

(71) Applicant: Dow AgroSciences LLC, Indianapolis, IN (US)

(72) Inventors: Manju Gupta, Carmel, IN (US); Sara Bennett, Indianapolis, IN (US); Navin Elango, Indianapolis, IN (US); Karthik Muthuraman, Indianapolis, IN (US); Jeffrey Beringer, Indianapolis, IN (US); Huixia Wu, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/604,510

(22) Filed: Jan. 23, 2015

(65) Prior Publication Data

US 2016/0237446 A1  Aug. 18, 2016

Related U.S. Application Data

(60) Provisional application No. 61/930,738, filed on Jan. 23, 2014.

(51) Int. Cl.
*C12N 15/82* (2006.01)

(52) U.S. Cl.
CPC ..... *C12N 15/8223* (2013.01); *C12N 15/8218* (2013.01); *C12N 15/8271* (2013.01); *C12N 15/8279* (2013.01)

(58) Field of Classification Search
None
See application file for complete search history.

(56) References Cited

U.S. PATENT DOCUMENTS 5,656,496 A * 8/1997 Quail ................ C12N 15/8237
435/320.1

* cited by examiner

*Primary Examiner* — Cathy Kingdon Worley
(74) *Attorney, Agent, or Firm* — Sean M. Russell; James Daly, IV; Magleby Cataxinos & Greenwood

(57) ABSTRACT

Provided are constructs and methods for expressing a transgene in plant cells and/or plant tissues using *Zea mays* chlorophyll a/b binding gene regulatory elements.

22 Claims, 10 Drawing Sheets

Fig. 2:

```
                                              1                              30
Modified promoter (SEQ ID NO:3)    (1)   GCACAAAATACATAAAACTAGATTAGAAAA
Full length promoter (SEQ ID NO:1) (1)   GCACAAAATACATAAAACTAGATTAGAAAA
                                              31                             60
Modified promoter (SEQ ID NO:3)    (31)  GGAAGAGAATACGCCAAATTGCAGCTTAAT
Full length promoter (SEQ ID NO:1) (31)  GGAAGAGAATACGCCAAATTGCAGCTTAAT
                                              61                             90
Modified promoter (SEQ ID NO:3)    (61)  CAATTAGACGATTTAGTCCTGTTTTTACGA
Full length promoter (SEQ ID NO:1) (61)  CAATTAGACGATTTAGTCCTGTTTTTACGA
                                              91                            120
Modified promoter (SEQ ID NO:3)    (91)  AACAATTGTTTAAGATAACAT---------
Full length promoter (SEQ ID NO:1) (91)  AACAATTGTTTAAGATAACATTAGGACATG
                                              121                           150
Modified promoter (SEQ ID NO:3)    (112) ------------------------------
Full length promoter (SEQ ID NO:1) (121) TACAATATGTGTCTTTGGATGTGTTTAAGG
                                              151                           180
Modified promoter (SEQ ID NO:3)    (112) ------------------------------
Full length promoter (SEQ ID NO:1) (151) AGTAAATGTAAAAAAAATAGATACGTCTCT
                                              181                           210
Modified promoter (SEQ ID NO:3)    (112) ------------------------------
Full length promoter (SEQ ID NO:1) (181) TAACGAAGTCATTGTGTCTTGGCTCTATGC
                                              211                           240
Modified promoter (SEQ ID NO:3)    (112) ------------------------------
Full length promoter (SEQ ID NO:1) (211) TCGAGACGGAGAAATAGCTAATTGATTAAT
                                              241                           270
Modified promoter (SEQ ID NO:3)    (112) ------------------------------
Full length promoter (SEQ ID NO:1) (241) TTAATTTATTGAATGTTCTTATTGGTGTAA
                                              271                           300
Modified promoter (SEQ ID NO:3)    (112) ------------------GGCCTTATACTT
Full length promoter (SEQ ID NO:1) (271) TGAATATAGTAAGGCACTGGCCTTATACTT
                                              301                           330
Modified promoter (SEQ ID NO:3)    (124) GGAGTTTGGCATGTCTTATGCTATGTTGCA
Full length promoter (SEQ ID NO:1) (301) GGAGTTTGGCATGTCTTATGCTATGTTGCA
                                              331                           360
Modified promoter (SEQ ID NO:3)    (154) AACAGGCCCGGTCTTGACATTTCGGGGCCC
Full length promoter (SEQ ID NO:1) (331) AACAGGCCCGGTCTTGACATTTCGGGGCCC
                                              361                           390
Modified promoter (SEQ ID NO:3)    (184) CTAAGAGAAAATTTATATAGAGGTCCTATA
Full length promoter (SEQ ID NO:1) (361) CTAAGAGAAAATTTATATAGAGGTCCTATA
                                              391                           420
Modified promoter (SEQ ID NO:3)    (214) CGAAAATTTGAGTCTGTTATTTTTTCAACT
Full length promoter (SEQ ID NO:1) (391) CGAAAATTTGAGTCTGTTATTTTTTCAACT
                                              421                           450
Modified promoter (SEQ ID NO:3)    (244) TTTAAATAATATATGAAAAATAAAAAATTG
Full length promoter (SEQ ID NO:1) (421) TTTAAATAATATATGAAAAATAAAAAATTG
                                              451                           480
Modified promoter (SEQ ID NO:3)    (274) ATGATTTACATAATTTTATTCAAAATGATA
Full length promoter (SEQ ID NO:1) (451) ATGATTTACATAATTTTATTCAAAATGATA
                                              481                           510
Modified promoter (SEQ ID NO:3)    (304) TGACTGGAAATATTGTTACAGTATTTTATG
Full length promoter (SEQ ID NO:1) (481) TGACTGGAAATATTGTTACAGTATTTTATG
                                              511                           540
Modified promoter (SEQ ID NO:3)    (334) AGTCGTAAAATTATATAAATTATGTAATAT
```

Fig. 2 cont.

```
Full length promoter (SEQ ID NO:1)   (511) AGTCGTAAAATTATATAAATTATGTAATAT
                                            541                          570
   Modified promoter (SEQ ID NO:3)   (364) ACATTTGTTTTGACTTTTGAGAGAGTATTT
Full length promoter (SEQ ID NO:1)   (541) ACATTTGTTTTGACTTTTGAGAGAGTATTT
                                            571                          600
   Modified promoter (SEQ ID NO:3)   (394) TTACTTTTAATTTGTCAAACTAGCCTAAAC
Full length promoter (SEQ ID NO:1)   (571) TTACTTTTAATTTGTCAAACTAGCCTAAAC
                                            601                          630
   Modified promoter (SEQ ID NO:3)   (424) CTTAAAATACACAGTAAACCAAATCTAAAT
Full length promoter (SEQ ID NO:1)   (601) CTTAAAATACACAGTAAACCAAATCTAAAT
                                            631                          660
   Modified promoter (SEQ ID NO:3)   (454) ACATTAGATCAAATTTTCTGAAAATAAAGT
Full length promoter (SEQ ID NO:1)   (631) ACATTAGATCAAATTTTCTGAAAATAAAGT
                                            661                          690
   Modified promoter (SEQ ID NO:3)   (484) TCAGCAAACTAAACTAGGATTAATCAATGT
Full length promoter (SEQ ID NO:1)   (661) TCAGCAAACTAAACTAGGATTAATCAATGT
                                            691                          720
   Modified promoter (SEQ ID NO:3)   (514) AGGTTATTAGGGTCGACCCTTCGGTAGGCT
Full length promoter (SEQ ID NO:1)   (691) AGGTTATTAGGGTCGACCCTTCGGTAGGCT
                                            721                          750
   Modified promoter (SEQ ID NO:3)   (544) AGAATTAAGCAACGCGATAGGCACAGGTGT
Full length promoter (SEQ ID NO:1)   (721) AGAATTAAGCAACGCGATAGGCACAGGTGT
                                            751                          780
   Modified promoter (SEQ ID NO:3)   (574) ACAACACCTTTCGTCCTTCCCACGTCAAT-
Full length promoter (SEQ ID NO:1)   (751) ACAACACCTTTCGTCCTTCCCACGTCAATT
                                            781                          810
   Modified promoter (SEQ ID NO:3)   (603) ------------------------------
Full length promoter (SEQ ID NO:1)   (781) TTAGGGCCTGTTTGGTTCACGGCTAATTAT
                                            811                          840
   Modified promoter (SEQ ID NO:3)   (603) ------------------------------
Full length promoter (SEQ ID NO:1)   (811) GCCACACTTTGCCTAAGGTTAGTCGTCCGA
                                            841                          870
   Modified promoter (SEQ ID NO:3)   (603) ------------------------------
Full length promoter (SEQ ID NO:1)   (841) ATTGAAGAACTAACCTTATGCAGAAAAGTT
                                            871                          900
   Modified promoter (SEQ ID NO:3)   (603) ------------------------------
Full length promoter (SEQ ID NO:1)   (871) AGGCAAAGTATGGCAAGTTAGGTAGTAAAC
                                            901                          930
   Modified promoter (SEQ ID NO:3)   (603) ----------AAAGTATTTGTCATCAAGCA
Full length promoter (SEQ ID NO:1)   (901) CAAACAGGCCAAAGTATTTGTCATCAAGCA
                                            931                          960
   Modified promoter (SEQ ID NO:3)   (623) GACGGTTGCGCGACCTCAAAGAGATGATTG
Full length promoter (SEQ ID NO:1)   (931) GACGGTTGCGCGACCTCAAAGAGATGATTG
                                            961                          990
   Modified promoter (SEQ ID NO:3)   (653) CTAGAAAATAAAGAGACGCAACAAAAGAAT
Full length promoter (SEQ ID NO:1)   (961) CTAGAAAATAAAGAGACGCAACAAAAGAAT
                                            991                         1020
   Modified promoter (SEQ ID NO:3)   (683) GAAAATATAGATTTATCTATAACTTATATG
Full length promoter (SEQ ID NO:1)   (991) GAAAATATAGATTTATCTATAACTTATATG
                                           1021                         1050
   Modified promoter (SEQ ID NO:3)   (713) CATTTGATATAAGATAGATAAATGGGAGCC
Full length promoter (SEQ ID NO:1)  (1021) CATTTGATATAAGATAGATAAATGGGAGCC
                                           1051                         1080
   Modified promoter (SEQ ID NO:3)   (743) CTACGAACCTTGAGGCTCTGAGCAGTCGCA
Full length promoter (SEQ ID NO:1)  (1051) CTACGAACCTTGAGGCTCTGAGCAGTCGCA
                                           1081                         1110
   Modified promoter (SEQ ID NO:3)   (773) TATCCTGCACACCCTTGGCGCCGGCCCTGG
```

Fig. 2 cont.

```
Full length promoter (SEQ ID NO:1)  (1081) TATCCTGCACACCCTTGGCGCCGGCCCTGG
                                           1111                          1140
   Modified promoter (SEQ ID NO:3)   (803) TTGCAAATATGCAATTGTGTCCTTATCCGC
Full length promoter (SEQ ID NO:1)  (1111) TTGCAAATATGCAATTGTGTCCTTATCCGC
                                           1141                          1170
   Modified promoter (SEQ ID NO:3)   (833) GACTGGTCACGAGGCTAGGATTGATCGAAA
Full length promoter (SEQ ID NO:1)  (1141) GACTGGTCACGAGGCTAGGATTGATCGAAA
                                           1171                          1200
   Modified promoter (SEQ ID NO:3)   (863) GCTGCCGATGACAAATGGCAAGCGGCGCCAT
Full length promoter (SEQ ID NO:1)  (1171) GCTGCCGATGACAAATGGCAAGCGGCGCCAT
                                           1201                          1230
   Modified promoter (SEQ ID NO:3)   (893) GCTGTGGCCTTTTTTTTACGGTCTGTCAGG
Full length promoter (SEQ ID NO:1)  (1201) GCTGTGGCCTTTTTTTTACGGTCTGTCAGG
                                           1231                          1260
   Modified promoter (SEQ ID NO:3)   (923) ACAACTGAAAAGTTACAAATTTATAGTGGT
Full length promoter (SEQ ID NO:1)  (1231) ACAACTGAAAAGTTACAAATTTATAGTGGT
                                           1261                          1290
   Modified promoter (SEQ ID NO:3)   (953) TGTAAACAGCAACACGTTAAAAAGTCGATT
Full length promoter (SEQ ID NO:1)  (1261) TGTAAACAGCAACACGTTAAAAAGTCGATT
                                           1291                          1320
   Modified promoter (SEQ ID NO:3)   (983) ATCAGTTTCACAGAAAGAGGTCGTTAAAAC
Full length promoter (SEQ ID NO:1)  (1291) ATCAGTTTCACAGAAAGAGGTCGTTAAAAC
                                           1321                          1350
   Modified promoter (SEQ ID NO:3)  (1013) CGCCAGCAAGCTTGTTTCACTATCAGTCTG
Full length promoter (SEQ ID NO:1)  (1321) CGCCAGCAAGCTTGTTTCACTATCAGTCTG
                                           1351                          1380
   Modified promoter (SEQ ID NO:3)  (1043) TCGCTAAGACAATCTCTTTCACCAAAAATA
Full length promoter (SEQ ID NO:1)  (1351) TCGCTAAGACAATCTCTTTCACCAAAAATA
                                           1381                          1410
   Modified promoter (SEQ ID NO:3)  (1073) CAATTTGCTTTCTTGCCGTTGCTTCAAGTG
Full length promoter (SEQ ID NO:1)  (1381) CAATTTGCTTTCTTGCCGTTGCTTCAAGTG
                                           1411                          1440
   Modified promoter (SEQ ID NO:3)  (1103) AAAATCT-----------------------
Full length promoter (SEQ ID NO:1)  (1411) AAAATCTTAATGTTTTAAATTAAAATATGT
                                           1441                          1470
   Modified promoter (SEQ ID NO:3)  (1110) ------------------------------
Full length promoter (SEQ ID NO:1)  (1441) GGCTCTACGTAGGAAAAAATAATTCAATCG
                                           1471                          1500
   Modified promoter (SEQ ID NO:3)  (1110) ------------------------------
Full length promoter (SEQ ID NO:1)  (1471) AGTCTCATTTCATAAAAAAAATTTGGTCAA
                                           1501                          1530
   Modified promoter (SEQ ID NO:3)  (1110) ------------------------------
Full length promoter (SEQ ID NO:1)  (1501) AAAATTATACACCATCTCGCTCAAGTGACT
                                           1531                          1560
   Modified promoter (SEQ ID NO:3)  (1110) ------------------------------
Full length promoter (SEQ ID NO:1)  (1531) CAAATATACTAAACGGTACTGAGCTGTCTT
                                           1561                          1590
   Modified promoter (SEQ ID NO:3)  (1110) ------------------------------
Full length promoter (SEQ ID NO:1)  (1561) ATAATATAAATTTGATTTACTGTTAGAATA
                                           1591                          1620
   Modified promoter (SEQ ID NO:3)  (1110) ------------------------------
Full length promoter (SEQ ID NO:1)  (1591) TGATGTTTTATGAGTGCACTAAATTCTATA
                                           1621                          1650
   Modified promoter (SEQ ID NO:3)  (1110) ------------------------------
Full length promoter (SEQ ID NO:1)  (1621) AAATATATTTATTTTTAAATTATAAGATAT
                                           1651                          1680
   Modified promoter (SEQ ID NO:3)  (1110) ----------------------GAGCTAA
```

Fig. 2 cont.

```
Full length promoter (SEQ ID NO:1)  (1651) TTTTATAGGTCTGCTCTTAGAGAGAGCTAA
                                            1681                          1710
   Modified promoter (SEQ ID NO:3)  (1117) AAAAGAGAGAGGCTGTCTGAAGAAAAATCC
Full length promoter (SEQ ID NO:1)  (1681) AAAAGAGAGAGGCTGTCTGAAGAAAAATCC
                                            1711                          1740
   Modified promoter (SEQ ID NO:3)  (1147) ATAACCAACGCAAAATCCCGGGCGCCCAAT
Full length promoter (SEQ ID NO:1)  (1711) ATAACCAACGCAAAATCCCGGGCGCCCAAT
                                            1741                          1770
   Modified promoter (SEQ ID NO:3)  (1177) CAGCCTTCTCCGCGGAGATTCCTAGCCTCA
Full length promoter (SEQ ID NO:1)  (1741) CAGCCTTCTCCGCGGAGATTCCTAGCCTCA
                                            1771                          1800
   Modified promoter (SEQ ID NO:3)  (1207) GCCAGAGCTACCTCATCTGCGTGAGGCTCC
Full length promoter (SEQ ID NO:1)  (1771) GCCAGAGCTACCTCATCTGCGTGAGGCTCC
                                            1801                          1830
   Modified promoter (SEQ ID NO:3)  (1237) GGTGGCGCCAACTGTTCCCGGCATCCCCGAC
Full length promoter (SEQ ID NO:1)  (1801) GGTGGCGCCAACTGTTCCCGGCATCCCCGAC
                                            1831                          1860
   Modified promoter (SEQ ID NO:3)  (1267) GCACCAATGGCATCCGAGCAACAGATCTTT
Full length promoter (SEQ ID NO:1)  (1831) GCACCAATGGCATCCGAGCAACAGATCTTT
                                            1861                          1890
   Modified promoter (SEQ ID NO:3)  (1297) TCTGCAACAACGCTTCGCGTCGCGGCGGTG
Full length promoter (SEQ ID NO:1)  (1861) TCTGCAACAACGCTTCGCGTCGCGGCGGTG
                                            1891                          1920
   Modified promoter (SEQ ID NO:3)  (1327) TTTCCCTCCATCTGCTCTGCTCTTTAAATA
Full length promoter (SEQ ID NO:1)  (1891) TTTCCCTCCATCTGCTCTGCTCTTTAAATA
                                            1921                          1950
   Modified promoter (SEQ ID NO:3)  (1357) CCTCCGTCGTCTCCTCGTCTCCACAGCATC
Full length promoter (SEQ ID NO:1)  (1921) CCTCCGTCGTCTCCTCGTCTCCACAGCATC
                                            1951                          1980
   Modified promoter (SEQ ID NO:3)  (1387) TCAAGTCTTCACACTCCTCGCCATCACATA
Full length promoter (SEQ ID NO:1)  (1951) TCAAGTCTTCACACTCCTCGCCATCACATA
                                            1981                      2006
   Modified promoter (SEQ ID NO:3)  (1417) AAACCAGTGCAAGCAGAAGCAGCGCA
Full length promoter (SEQ ID NO:1)  (1981) AAACCAGTGCAAGCAGAAGCAGCGCA
```

ZEA MAYS PROMOTER FROM CHLOROPHYLL A/B BINDING PROTEIN GENE AND USES THEREOF

CROSS-REFERENCE TO RELATED APPLICATION

This application claims priority to U.S. Provisional Patent Application Ser. No. 61/930,738 filed Jan. 23, 2014, the disclosure of which is hereby incorporated herein in its entirety by this reference.

FIELD OF THE INVENTION

This invention is generally related to the field of plant molecular biology, and more specifically, to the field of expression of transgenes in plants.

BACKGROUND

Many plant species are capable of being transformed with transgenes to introduce agronomically desirable traits or characteristics. Plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation of the plant genome results in transgenic plants that possess desirable traits and phenotypes. However, mechanisms that allow the production of transgenic plant species to highly express multiple transgenes engineered as a trait stack are desirable.

Likewise, mechanisms that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Furthermore, it may be desirable to express a transgene in leaf and stem tissues of a plant.

Described herein are *Zea mays* chlorophyll a/b binding gene promoter regulatory elements. Further described are constructs and methods utilizing *Zea mays* chlorophyll a/b binding gene promoter regulatory elements.

SUMMARY

Disclosed herein are sequences, constructs, and methods for expressing a transgene in plant cells and/or plant tissues. In an embodiment the disclosure relates to a gene expression cassette comprising a promoter operably linked to a transgene, wherein the promoter comprises a polynucleotide that hybridizes under stringent conditions to a polynucleotide probe comprising a sequence identity of at least 90% to a complement of SEQ ID NO:2. In further embodiments, the promoter comprises a polynucleotide that has at least 90% sequence identity to SEQ ID NO:2. In additional embodiments, the promoter comprises a polynucleotide comprising an intron. In other embodiments, the intron has at least 90% sequence identity to SEQ ID NO:5. In an embodiment, the promoter comprises a polynucleotide that has at least 90% sequence identity to SEQ ID NO:1. In other embodiments, the operably linked transgene encodes a polypeptide or a small RNA. In a subsequent embodiment, the transgene is selected from the group consisting of insecticidal resistance transgene, herbicide tolerance transgene, nitrogen use efficiency transgene, water use efficiency transgene, nutritional quality transgene, DNA binding transgene, and selectable marker transgene. In yet another embodiment, the gene expression cassette further comprises a 3'-untranslated region. In an embodiment the 3'-untranslated region comprises a polynucleotide that has a sequence identity of at least 90% to SEQ ID NO:7 or SEQ ID NO:8. In yet another embodiment, the gene expression cassette further comprises a 5'-untranslated region. In another embodiment the 5'-untranslated region comprises a polynucleotide that has a sequence identity of at least 90% to SEQ ID NO:19. In an embodiment, a recombinant vector comprises the gene expression cassette. In a further aspect of the embodiment, the recombinant vector is selected from the group consisting of a plasmid, a cosmid, a bacterial artificial chromosome, a virus, and a bacteriophage. In an embodiment, a transgenic cell comprises the gene expression cassette. In a subsequent aspect of the embodiment, the cell is a transgenic plant cell. In an embodiment, a transgenic plant comprises the transgenic plant cell. In a further aspect of the embodiment, the transgenic plant is a monocotyledonous plant or dicotyledonous plant. In other aspects of the embodiment, the monocotyledonous plant is selected from the group consisting of a maize plant, a rice plant, and a wheat plant. In an embodiment, a transgenic seed is obtained from the transgenic plant. In a subsequent embodiment, the promoter is a tissue-preferred promoter. In an additional embodiment, the tissue-preferred promoter is a leaf, husk, stem, or silk tissue-preferred promoter. In yet another embodiment, the promoter comprises a polynucleotide sequence of nucleotides 1-1,887 of SEQ ID NO:2.

In an embodiment the disclosure relates to a transgenic cell comprising a synthetic polynucleotide that hybridizes under stringent conditions to a polynucleotide probe comprising a sequence identity of at least 90% to a complement of SEQ ID NO:2. In an additional embodiment, the synthetic polynucleotide has at least 90% sequence identity to SEQ ID NO:2. In additional embodiments, the synthetic polynucleotide comprises a polynucleotide comprising an intron. In other embodiments, the intron has a sequence identity of at least 90% to SEQ ID NO:5. In an embodiment, the synthetic polynucleotide comprises a polynucleotide with at least 90% sequence identity to SEQ ID NO:1. In a further embodiment, the transgenic cell is a transgenic plant cell. In a subsequent embodiment, the transgenic plant cell is produced by a plant transformation method. In an additional embodiment, the plant transformation method is selected from the group consisting of an *Agrobacterium*-mediated transformation method, a biolistics transformation method, a silicon carbide transformation method, a protoplast transformation method, and a liposome transformation method. In an embodiment, a transgenic plant comprises the transgenic plant cell. In a further embodiment, the transgenic plant is a monocotyledonous plant or dicotyledonous plant. In other embodiments, the monocotyledonous plant is selected from the group consisting of a maize plant, a rice plant, and a wheat plant. In an embodiment, a transgenic seed is obtained from the transgenic plant. In an additional embodiment, the promoter is a tissue-preferred promoter. In a subsequent embodiment, the tissue-preferred promoter is a leaf, husk, stem, or silk tissue-preferred promoter. In another embodiment, the synthetic polynucleotide comprises a polynucleotide sequence of nucleotides 1-1,887 of SEQ ID NO:2.

In an embodiment the disclosure relates to a purified polynucleotide promoter, wherein the promoter comprises a polynucleotide that hybridizes under stringent conditions to a polynucleotide probe comprising a sequence identity of at least 90% to a complement of SEQ ID NO:2. In further embodiments, the purified polynucleotide promoter has at least 90% sequence identity to SEQ ID NO:2. In additional embodiments, the purified polynucleotide promoter comprises a polynucleotide comprising an intron. In other embodiments, the intron has at least 90% sequence identity to SEQ ID NO:5. In an embodiment, the purified polynucleotide promoter comprises a polynucleotide with at least 90% sequence identity to SEQ ID NO:1. In another embodiment, the purified polynucleotide is operably linked to a transgene. In a subsequent embodiment, the operably linked transgene encodes a polypeptide or is a small RNA. In an embodiment, a gene expression cassette comprises the purified polynucleotide sequence operably linked to the transgene, which is operably linked to a 3'-untranslated region. In an embodiment the 3'-untranslated region comprises a polynucleotide that has a sequence identity of at least 90% to SEQ ID NO:7 or SEQ ID NO:8. In an embodiment, a gene expression cassette comprises the purified polynucleotide sequence operably linked to the transgene, wherein the purified polynucleotide is a 5'-untranslated region of SEQ ID NO:19. In another embodiment, the 5'-untranslated region comprises a polynucleotide that has a sequence identity of at least 90% to SEQ ID NO:19. In another embodiment, the transgene is selected from the group consisting of insecticidal resistance transgene, herbicide tolerance transgene, nitrogen use efficiency transgene, water use efficiency transgene, nutritional quality transgene, DNA binding transgene, and selectable marker transgene. In an embodiment, a recombinant vector comprises the gene expression cassette. In an additional embodiment, the recombinant vector is selected from the group consisting of a plasmid vector, a cosmid vector, and a BAC vector. In an embodiment, a transgenic cell comprises the gene expression cassette. In a subsequent embodiment the transgenic cell is a transgenic plant cell. In an embodiment, a transgenic plant comprises the transgenic plant cell. In an additional embodiment, the transgenic plant is a monocotyledonous plant. In yet a further embodiment, the monocotyledonous plant is selected from the group consisting of a maize plant, a wheat plant, and a rice plant. In an embodiment, a transgenic seed is obtained from the transgenic plant. In a subsequent embodiment, the purified polynucleotide sequence promotes tissue-preferred expression of a transgene. In an additional embodiment, the purified polynucleotide sequence promotes leaf, husk, stem, or silk tissue-preferred expression of a transgene. In other embodiments, the purified polynucleotide comprises a polynucleotide sequence of nucleotides 1-1,887 of SEQ ID NO:2.

In an embodiment the disclosure relates to a method for expressing a heterologous coding sequence in a transgenic plant, the method comprising:

a) transforming a plant cell with a gene expression cassette comprising a polynucleotide sequence comprising a sequence identity of at least 90% to SEQ ID NO:2 operably linked to the heterologous coding sequence, which is operably linked to a 3'-untranslated region;
b) isolating the transformed plant cell comprising the gene expression cassette;
c) regenerating the transformed plant cell into a transgenic plant; and,
d) obtaining the transgenic plant, wherein the transgenic plant comprises the gene expression cassette comprising the polynucleotide sequence comprising SEQ ID NO:2.

In additional embodiments, the polynucleotide sequence comprises an intron. In other embodiments, the intron has a sequence identity of at least 90% to SEQ ID NO:5. In an embodiment, the polynucleotide sequence has at least 90% sequence identity to SEQ ID NO:1. In a further embodiment, the heterologous coding sequence is selected from the group consisting of insecticidal resistance coding sequences, herbicide tolerance coding sequences, nitrogen use efficiency coding sequences, water use efficiency coding sequences, nutritional quality coding sequences, DNA binding coding sequences, and selectable marker coding sequences. In an additional embodiment, transforming of a plant cell utilizes a plant transformation method. In yet another embodiment, the plant transformation method is selected from the group consisting of an *Agrobacterium*-mediated transformation method, a biolistics transformation method, a silicon carbide transformation method, a protoplast transformation method, and a liposome transformation method. In other embodiments, the transgenic plant is a monocotyledonous transgenic plant or a dicotyledonous transgenic plant. In further embodiments, the monocotyledonous transgenic plant is selected from the group consisting of a maize plant, a wheat plant, and a rice plant. In an embodiment, a transgenic seed is obtained from the transgenic plant. In a further embodiment, the heterologous coding sequence is preferentially expressed in a tissue. In yet another embodiment, the heterologous coding sequence is expressed in a leaf, husk, stem, or silk tissue. In other embodiments, the polynucleotide comprises a sequence of nucleotides 1-1,887 of SEQ ID NO:2.

In an embodiment the disclosure relates to a method for isolating a polynucleotide sequence comprising a sequence identity of at least 90% to SEQ ID NO:2, the method comprising:

a) identifying the polynucleotide sequence comprising a sequence identity of at least 90% to SEQ ID NO:2;
b) producing a plurality of oligonucleotide primer sequences, wherein the oligonucleotide primer sequences bind to the polynucleotide sequence comprising a sequence identity of at least 90% to SEQ ID NO:2;
c) amplifying the polynucleotide sequence comprising a sequence identity of at least 90% to SEQ ID NO:2 from a DNA sample with oligonucleotide primer sequences selected from the plurality of oligonucleotide primer sequences; and,
d) isolating the polynucleotide sequence comprising a sequence identity of at least 90% to SEQ ID NO:2.

In additional embodiments, the polynucleotide sequence comprises an intron. In other embodiments, the intron has a sequence identity of at least 90% to SEQ ID NO:5. In an embodiment, the polynucleotide sequence has at least 90% sequence identity to SEQ ID NO:1. In an additional embodiment, the isolated polynucleotide sequence comprising a sequence identity of at least 90% to SEQ ID NO:2 is operably linked to a transgene. In a further embodiment, the operably linked transgene encodes a polypeptide. In an embodiment, a gene expression cassette comprises a polynucleotide sequence with at least 90% sequence identity to SEQ ID NO:2 operably linked to a transgene, wherein the transgene is operably linked to a 3'-untranslated region. In an embodiment the 3'-untranslated region comprises a polynucleotide that has a sequence identity of at least 90% to SEQ ID NO:7 or SEQ ID NO:8. In a further embodiment, the transgene is selected from the group consisting of insecticidal resistance coding sequences, herbicide tolerance coding sequences, nitrogen use efficiency coding sequences, water use efficiency coding sequences, nutritional quality coding sequences, DNA binding coding sequences, and selectable marker coding sequences. In an embodiment, a recombinant vector comprises the gene expression cassette. In a further embodiment, the vector is selected from the group consisting of a plasmid vector, a cosmid vector, and a BAC vector. In an embodiment, a transgenic cell comprises the gene expression cassette. In an additional embodiment, the transgenic cell is a transgenic plant cell. In an embodiment, a transgenic plant comprises the transgenic plant cell. In an additional embodiment, the transgenic plant is a monocotyledonous plant or a dicotyledonous plant. In a further embodiment, the monocotyledonous plant is selected from the group consisting of a maize plant, a wheat plant, and a rice plant. In an embodiment, a transgenic seed is obtained from the transgenic plant. In other embodiments, the isolated polynucleotide comprises a polynucleotie sequence of nucleotides 1-1,887 of SEQ ID NO:2.

In an embodiment the disclosure relates to a method for manufacturing a synthetic polynucleotide sequence comprising a sequence identity of at least 90% to SEQ ID NO:2, the method comprising:
a) identifying the polynucleotide sequence comprising SEQ ID NO:2;
b) isolating the polynucleotide sequence comprising SEQ ID NO:2;
c) defining a plurality of polynucleotide sequences that comprise a sequence identity of at least 90% to SEQ ID NO:2;
d) synthesizing a polynucleotide sequence comprising a sequence identity of at least 90% to SEQ ID NO:2; and,
e) manufacturing a synthetic polynucleotide sequence comprising a sequence identity of at least 90% to SEQ ID NO:2.

In a further embodiment, the synthesizing comprises:
a) identifying the polynucleotide sequence comprising a sequence identity of at least 90% to SEQ ID NO:2;
b) producing a plurality of oligonucleotide primer sequences, wherein the oligonucleotide primer sequences bind to the polynucleotide sequence comprising a sequence identity of at least 90% to SEQ ID NO:2;
c) ligating the plurality of oligonucleotide primer sequences to synthesize the polynucleotide sequence comprising a sequence identity of at least 90% to SEQ ID NO:2.

In additional embodiments, the synthesized polynucleotide sequence comprises an intron. In other embodiments, the intron has a sequence identity of at least 90% to SEQ ID NO:5. In an embodiment, the synthesized polynucleotide sequence has at least 90% sequence identity to SEQ ID NO:1. In an additional embodiment, the synthesized polynucleotide sequence comprises a sequence identity of at least 90% to SEQ ID NO:2 that is operably linked to a transgene. In yet another embodiment, the operably linked transgene encodes a polypeptide. In an embodiment, a gene expression cassette comprises the synthesized polynucleotide sequence comprising a sequence identity of at least 90% to SEQ ID NO:2 operably linked to the transgene, that is operably linked to a 3'-untranslated region. In an embodiment the 3'-untranslated region comprises a polynucleotide that has a sequence identity of at least 90% to SEQ ID NO:7 or SEQ ID NO:8. In yet another embodiment, the transgene is selected from the group consisting of insecticidal resistance transgene, herbicide tolerance transgene, nitrogen use efficiency transgene, water use efficiency transgene, nutritional quality transgene, DNA binding transgene, and selectable marker transgene. In an embodiment, a recombinant vector comprises the gene expression cassette. In an additional embodiment, the recombinant vector is selected from the group consisting of a plasmid vector, a cosmid vector, and a BAC vector. In an embodiment, a transgenic cell comprises the gene expression cassette. In a further embodiment, the transgenic cell is a transgenic plant cell. In an embodiment, a transgenic plant comprises the transgenic plant cell. In a further embodiment, the transgenic plant is a monocotyledonous plant. In other embodiments, the monocotyledonous plant is selected from the group consisting of a maize plant, a wheat plant, and a rice plant. In an embodiment, a transgenic seed is obtained from the transgenic plant. In other embodiments, the synthetic polynucleotide comprises a polynucleotide sequence of nucleotides 1-1,887 of SEQ ID NO:2.

In an embodiment, a construct includes a gene expression cassette comprising a *Zea mays* chlorophyll a/b binding gene promoter of SEQ ID NO:1, SEQ ID NO:2, SEQ ID NO:3, or SEQ ID NO:4. In an embodiment, a gene expression cassette includes a *Zea mays* chlorophyll a/b binding gene promoter of SEQ ID NO:1, SEQ ID NO:2, SEQ ID NO:3, or SEQ ID NO:4 operably linked to a transgene or a heterologous coding sequence. In an embodiment, a gene expression cassette includes a *Zea mays* chlorophyll a/b binding gene 3'-UTR of SEQ ID NO:7 or SEQ ID NO:8 operably linked to a transgene. In an embodiment, a gene expression cassette includes a *Zea mays* chlorophyll a/b binding gene 3'-UTR of SEQ ID NO:7 or SEQ ID NO:8 operably linked to a promoter. In a further embodiment, a gene expression cassette includes a *Zea mays* chlorophyll a/b binding gene 3'-UTR of SEQ ID NO:7 or SEQ ID NO:8 operably linked to a *Zea mays* chlorophyll a/b binding gene promoter of SEQ ID NO:1, SEQ ID NO:2, SEQ ID NO; 3, or SEQ ID NO:4. In an embodiment, a gene expression cassette includes a *Zea mays* chlorophyll a/b binding gene 5'-UTR of SEQ ID NO:19 operably linked to a transgene. In an embodiment, a gene expression cassette includes a *Zea mays* chlorophyll a/b binding gene 5'-UTR of SEQ ID NO:19 operably linked to a promoter. In a further embodiment, a gene expression cassette includes a *Zea mays* chlorophyll a/b binding gene 5'-UTR of SEQ ID NO:19 operably linked to a *Zea mays* chlorophyll a/b binding gene promoter of SEQ ID NO:1, SEQ ID NO:2, SEQ ID NO; 3, or SEQ ID NO:4. In an embodiment, a gene expression cassette includes a *Zea mays* chlorophyll a/b binding gene intron of SEQ ID NO:5 or SEQ ID NO:6 operably linked to a transgene. In an embodiment, a gene expression cassette includes a *Zea mays* chlorophyll a/b binding gene intron of SEQ ID NO:5 or SEQ ID NO:6 operably linked to a promoter. In an embodiment, a gene expression cassette includes a *Zea mays* chlorophyll a/b binding gene promoter of SEQ ID NO:1, SEQ ID NO:2, SEQ ID NO:3, or SEQ ID NO:4 operably linked to a transgene or a heterologous coding sequence. In an embodiment, a gene expression cassette includes at least one, two, three, four, five, six, seven, eight, nine, ten, or more transgenes.

In an embodiment, a gene expression cassette includes independently a) a *Zea mays* chlorophyll a/b binding gene promoter of SEQ ID NO:1, SEQ ID NO:2, SEQ ID NO:3, or SEQ ID NO:4, b) a *Zea mays* chlorophyll a/b binding gene intron of SEQ ID NO:5 or SEQ ID NO:6, c) a *Zea mays* chlorophyll a/b binding gene 3'-UTR of SEQ ID NO:7 or SEQ ID NO:8 and d) a *Zea mays* chlorophyll a/b binding gene 5'-UTR of SEQ ID NO:19.

Methods of growing plants expressing a transgene using *Zea mays* chlorophyll a/b binding gene promoters of SEQ ID NO:1, SEQ ID NO:2, SEQ ID NO:3, or SEQ ID NO:4; introns of SEQ ID NO:5 or SEQ ID NO:6; 3'-UTRs of SEQ ID NO:7 or SEQ ID NO:8; and 5'-UTR of SEQ ID NO:19 are disclosed herein. Methods of culturing plant tissues and cells expressing a transgene using the *Zea mays* chlorophyll a/b binding gene promoters of SEQ ID NO:1, SEQ ID NO:2, SEQ ID NO:3, or SEQ ID NO:4; introns of SEQ ID NO:5 or SEQ ID NO:6; 3'-UTRs of SEQ ID NO:7 or SEQ ID NO:8; and 5'-UTR of SEQ ID NO:19 are also disclosed herein. In an embodiment, methods as disclosed herein include tissue-specific gene expression in plant leaves and stems.

In an embodiment, a gene expression cassette includes a promoter polynucleotide sequence of SEQ ID NO:1, SEQ ID NO:2, SEQ ID NO:3, or SEQ ID NO:4 that was obtained from *Zea mays* chlorophyll a/b binding gene.

BRIEF DESCRIPTION OF THE DRAWINGS

FIG. 2 shows an alignment of the full length *Zea mays* chlorophyll a/b binding gene promoter (SEQ ID NO:1) as compared to the modified *Zea mays* chlorophyll a/b binding gene promoter (SEQ ID NO:3), this alignment shows the repeated polynucleotide sequences that were removed to produce the modified *Zea mays* chlorophyll a/b binding gene promoter sequence.

DETAILED DESCRIPTION

Definitions

Figure 1:
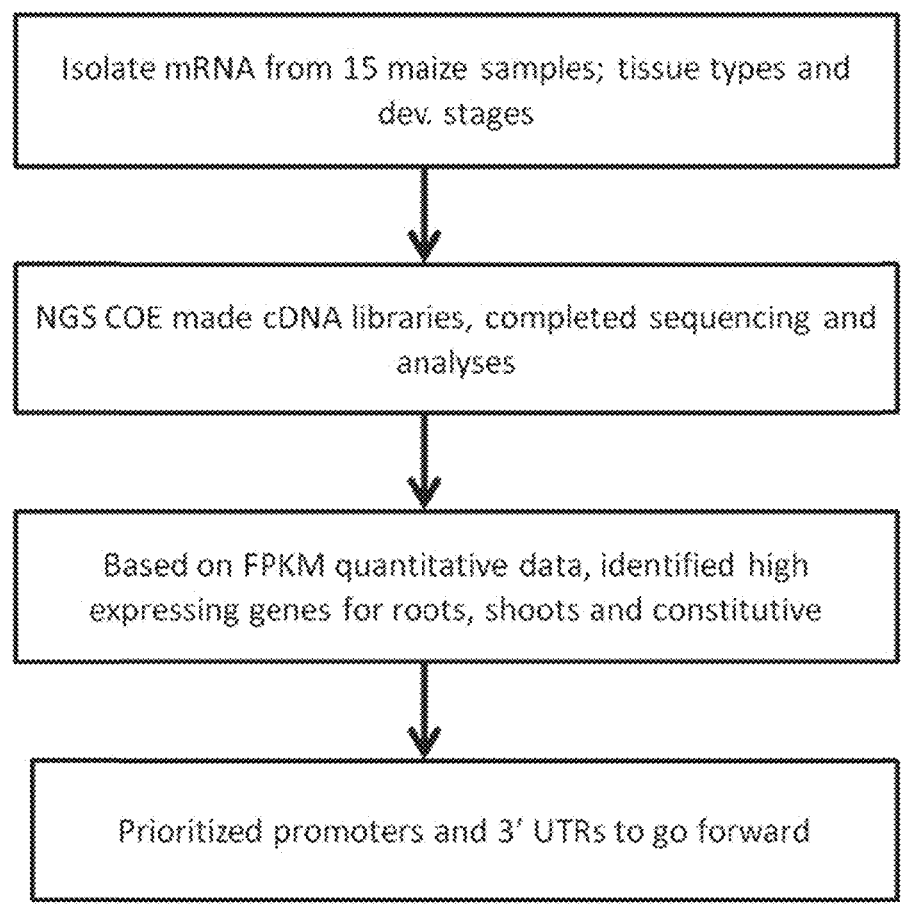
FIG. 1 is a schematic flow chart displaying the process of identifying high expressing genes in maize using a transcriptional profiling approach with Next Generation Sequencing (NGS).
Figure 3:
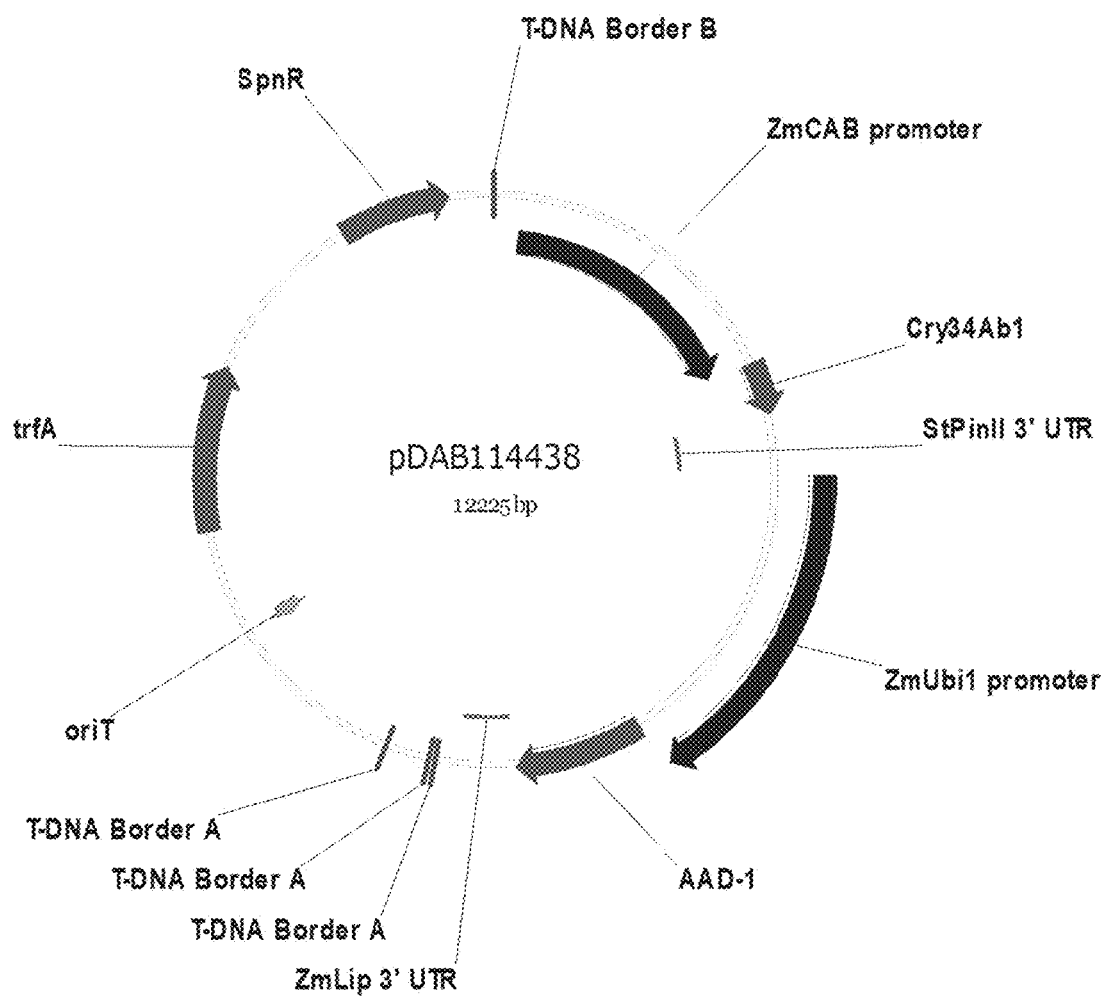
FIG. 3 shows the vector plasmid map of pDAB114438 depicting a gene expression cassette comprising the full length *Zea mays* chlorophyll a/b binding gene promoter regulatory elements (labeled as "ZmCAB promoter") controlling the expression of a cry34Ab1 reporter gene.
Figure 4:
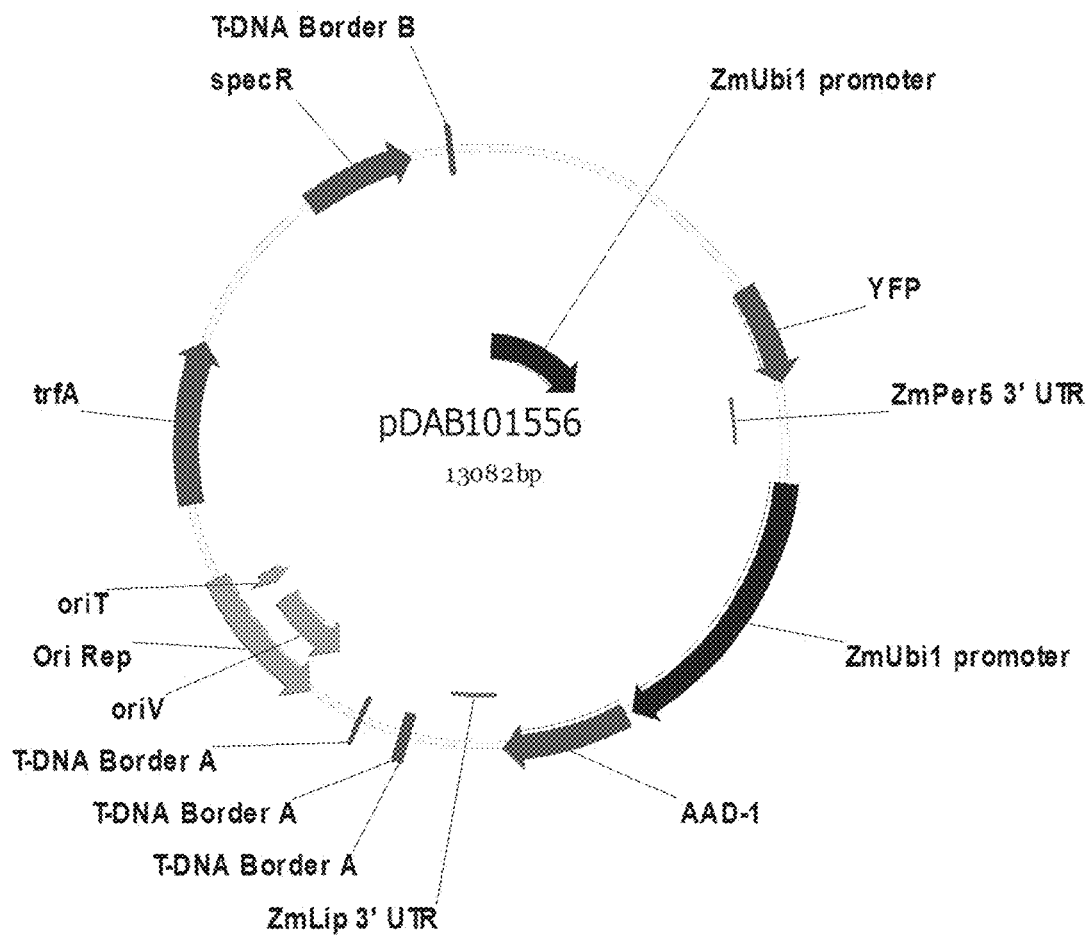
FIG. 4 shows a map of pDAB101556 control vector containing an yfp reporter gene in place of the cry34Ab1 reporter gene present in the test promoter construct, pDAB114438, as the gene of interest. The yfp gene expression was driven by the *Zea mays* ubiquitin-1 (ZmUbi1) promoter and terminated by the *Zea mays* Per5 (ZmPer5) 3'-UTR.
Figure 5:
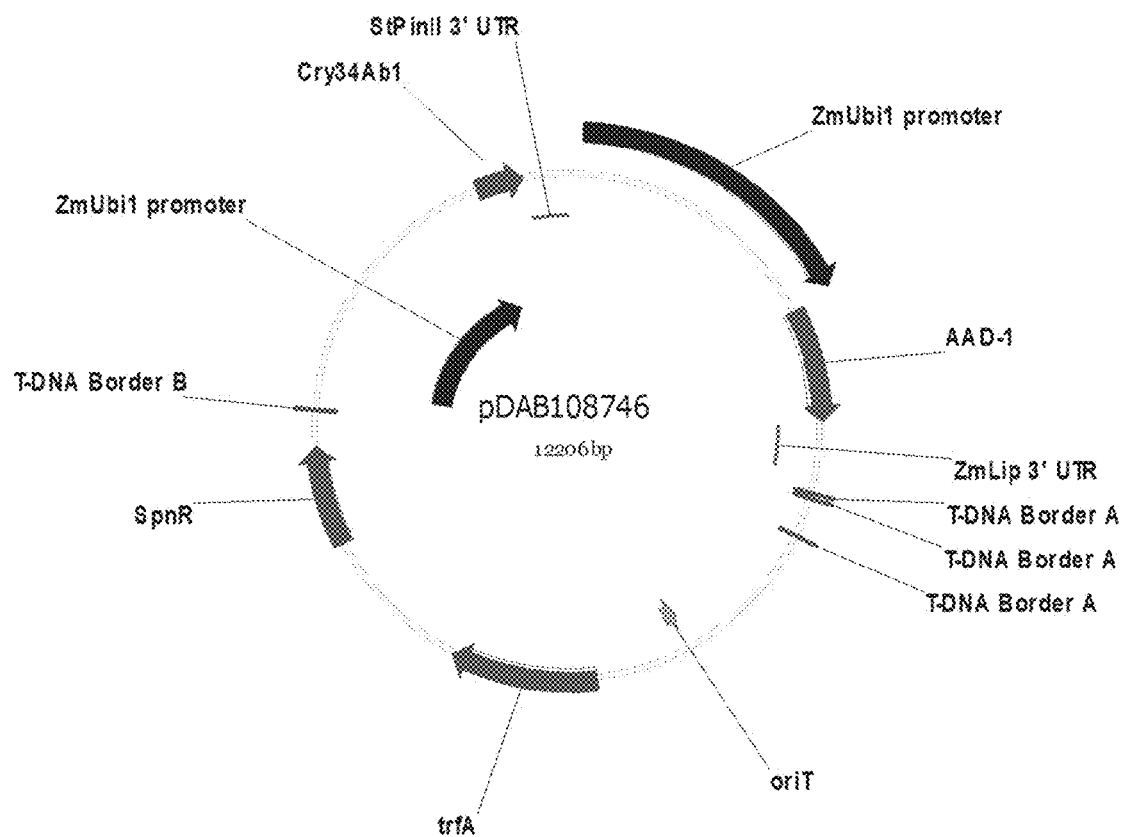
FIG. 5 shows a map of pDAB108746, a positive control vector containing the cry34Ab1 reporter gene driven by the ZmUbi1 promoter and terminated by the *Solanum tuberosum* PinII (StPinII) 3'-UTR.
Figure 6:
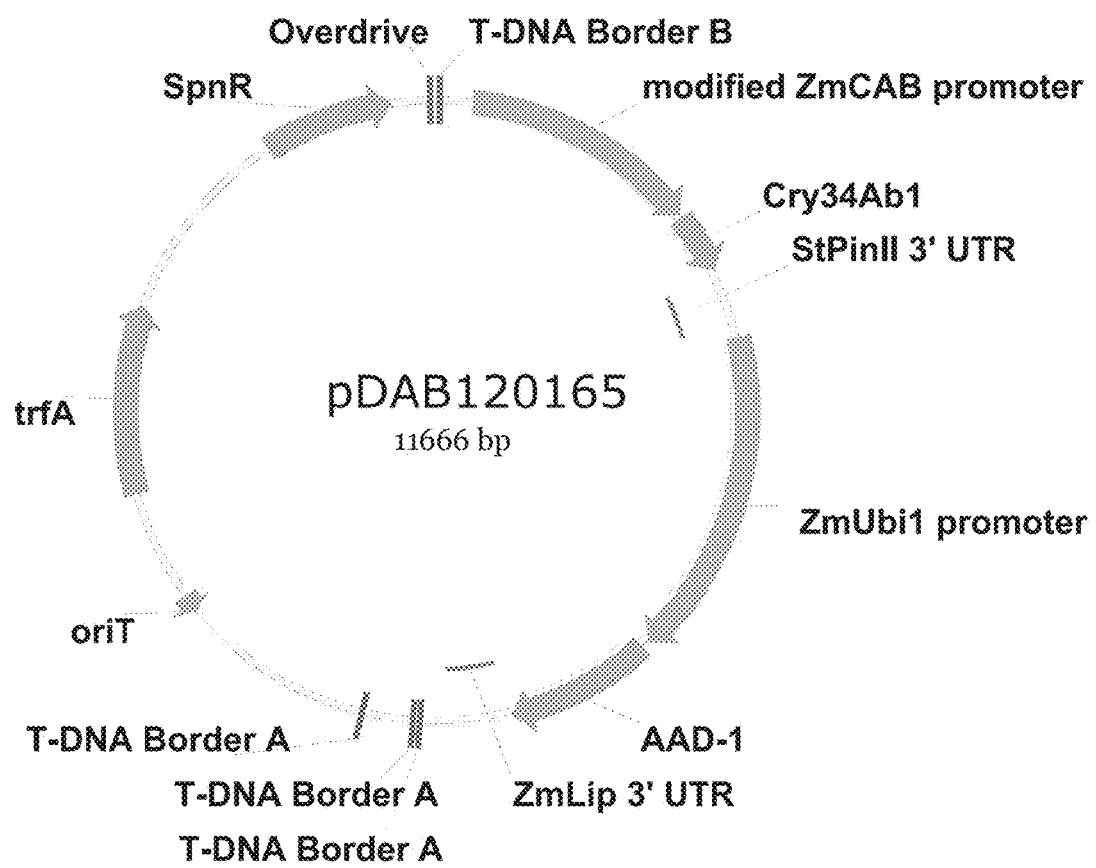
FIG. 6 shows the vector plasmid map of pDAB120165 depicting a gene expression cassette comprising the modified *Zea mays* chlorophyll a/b binding gene promoter regulatory elements controlling the expression of a cry34Ab1 reporter gene.
Figure 7:
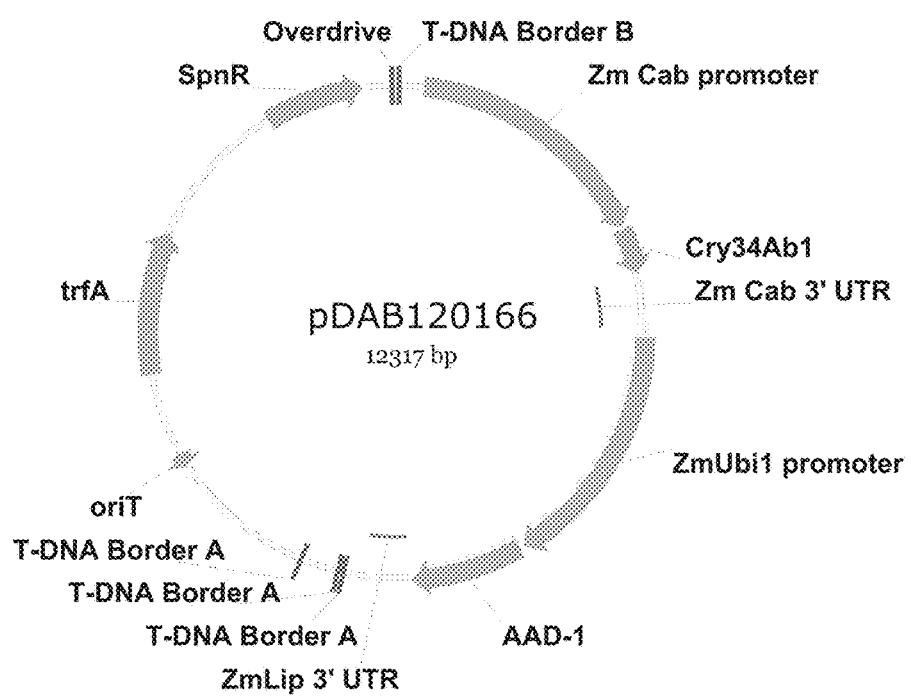
FIG. 7 shows the vector plasmid map of pDAB120166 depicting a gene expression cassette comprising the full length *Zea mays* chlorophyll a/b binding gene promoter (labeled as "ZmCAB promoter") and modified *Zea mays* chlorophyll a/b binding gene 3' UTR (SEQ ID No. 8) regulatory elements controlling the expression of a cry34Ab1 reporter gene.

As used herein, the articles, "a," "an," and "the" include plural references unless the context clearly and unambiguously dictates otherwise.

As used herein, the term "backcrossing" refers to a process in which a breeder crosses hybrid progeny back to one of the parents, for example, a first generation hybrid F1 with one of the parental genotypes of the F1 hybrid.

As used herein, the term "intron" refers to any nucleic acid sequence comprised in a gene (or expressed nucleotide sequence of interest) that is transcribed but not translated. Introns include untranslated nucleic acid sequence within an expressed sequence of DNA, as well as corresponding sequence in RNA molecules transcribed therefrom.

A construct described herein can also contain sequences that enhance translation and/or mRNA stability such as introns. An example of one such intron is the first intron of gene II of the histone variant of *Arabidopsis thaliana* or any other commonly known intron sequence. Introns can be used in combination with a promoter sequence to enhance translation and/or mRNA stability.

As used herein, the terms "5' untranslated region" or "5'-UTR" refer to an untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "3' untranslated region" or "3'-UTR" refers to an untranslated segment in a 3' terminus of the pre-mRNAs or mature mRNAs. For example, on mature mRNAs this region harbors the poly-(A) tail and is known to have many roles in mRNA stability, translation initiation, and mRNA export.

As used herein, the term "polyadenylation signal" refers to a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) *Plant Physiology* 138(3); 1457-1468.

As used herein, the term "isolated" refers to a biological component (including a nucleic acid or protein) that has been separated from other biological components in the cell of the organism in which the component naturally occurs (i.e., other chromosomal and extra-chromosomal DNA).

As used herein, the term "purified" in reference to nucleic acid molecules does not require absolute purity (such as a homogeneous preparation); instead, it represents an indication that the sequence is relatively more pure than in its native cellular environment (compared to the natural level this level should be at least 2-5 fold greater, e.g., in terms of concentration or gene expression levels). The DNA molecules may be obtained directly from total DNA or from total RNA. In addition, cDNA clones are not naturally occurring, but rather are preferably obtained via manipulation of a partially purified, naturally occurring substance (messenger RNA). The construction of a cDNA library from mRNA involves the creation of a synthetic substance (cDNA). Individual cDNA clones can be purified from the synthetic library by clonal selection of the cells carrying the cDNA library. Thus, the process which includes the construction of a cDNA library from mRNA and purification of distinct cDNA clones yields an approximately $10^6$-fold purification of the native message. Likewise, a promoter DNA sequence could be cloned into a plasmid. Such a clone is not naturally occurring, but rather is preferably obtained via manipulation of a partially purified, naturally occurring substance such as a genomic DNA library. Thus, purification of at least one order of magnitude, and in some embodiments two or three orders, and in other embodiments four or five or more orders of magnitude is favored in these techniques.

Similarly, purification represents an indication that a chemical or functional change in the component DNA sequence has occurred. Nucleic acid molecules and proteins that have been "purified" include nucleic acid molecules and proteins purified by standard purification methods. The term "purified" also embraces nucleic acids and proteins prepared by recombinant DNA methods in a host cell (e.g., plant cells), as well as chemically-synthesized nucleic acid molecules, proteins, and peptides.

The term "recombinant" means a cell or organism in which genetic recombination has occurred. It also includes a molecule (e.g., a vector, plasmid, nucleic acid, polypeptide, or a small RNA) that has been artificially or synthetically (i.e., non-naturally) altered by human intervention. The alteration can be performed on the molecule within, or removed from, its natural environment or state.

As used herein, the term "expression" refers to the process by which a polynucleotide is transcribed into mRNA (including small RNA molecules) and/or the process by which the transcribed mRNA (also referred to as "transcript") is subsequently translated into peptides, polypeptides, or proteins. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the terms "homology-based gene silencing" or "HBGS" are generic terms that include both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. Involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes.

As used herein, the terms "nucleic acid molecule," "nucleic acid," or "polynucleotide" (all three terms are synonymous with one another) refer to a polymeric form of nucleotides, which may include both sense and anti-sense strands of RNA, cDNA, genomic DNA, and synthetic forms, and mixed polymers thereof. "A nucleotide" may refer to a ribonucleotide, deoxyribonucleotide, or a modified form of either type of nucleotide. A nucleic acid molecule is usually at least 10 bases in length, unless otherwise specified. The terms may refer to a molecule of RNA or DNA of indeterminate length. The terms include single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the term "base position" refers to the location of a given base or nucleotide residue within a designated nucleic acid. A designated nucleic acid may be defined by alignment with a reference nucleic acid.

As used herein, the term "hybridization" refers to a process where polynucleotides or oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and bonding of a pyrimidine to a purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the terms "specifically hybridizable" and "specifically complementary" refers to a sufficient degree of complementarity such that stable and specific binding occurs between a polynucleotide/oligonucleotide and the DNA or RNA target. Oligonucleotides/polynucleotides need not be 100% complementary to the target sequence to specifically hybridize. An oligonucleotide/polynucleotide is specifically hybridizable when binding of the oligonucleotide/polynucleotide to the target DNA or RNA molecule interferes with the normal function of the target DNA or RNA, and there is sufficient degree of complementarity to avoid non-specific binding of an oligonucleotide/polynucleotide to non-target sequences under conditions where specific binding is desired, for example under physiological conditions in the case of in vivo assays or systems. Such binding is referred to as specific hybridization. Hybridization conditions resulting in particular degrees of stringency will vary depending upon the nature of the chosen hybridization method and the composition and length of the hybridizing nucleic acid sequences. Generally, the temperature of hybridization and the ionic strength (especially $Na^+$ and/or $Mg^{2+}$ concentration) of a hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N. Y., 1989.

As used herein, the term "stringent conditions" encompasses conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes. The following are representative, non-limiting hybridization conditions:

Very High Stringency: hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2-3×SSC buffer at room temperature to 55° C. for 20-30 minutes each.

In an embodiment, specifically hybridizable nucleic acid molecules can remain bound under very high stringency hybridization conditions. In an embodiment, specifically hybridizable nucleic acid molecules can remain bound under high stringency hybridization conditions. In an embodiment, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in polymerase chain reaction, a technique for the amplification of small DNA sequences. In polymerase chain reaction, an oligonucleotide is typically referred to as a "primer" which allows a DNA polymerase to extend the oligonucleotide and replicate the complementary strand.

As used herein, the terms "Polymerase Chain Reaction" or "PCR" refer to a procedure or technique in which minute amounts of nucleic acid, RNA and/or DNA, are amplified as described in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, N.Y., 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, that may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide or polynucleotide sequence that hybridizes to a target sequence. In the TAQMAN® or TAQMAN®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides.

In the Southern blot assay procedure, the probe hybridizes to a DNA fragment that is attached to a membrane. In such an assay the probe includes about ten nucleotides, about 100 nucleotides, about 250 nucleotides, about 500 nucleotides, about 1,000 nucleotides, about 2,500 nucleotides, or about 5,000 nucleotides. In some embodiments, a probe includes from about 500 nucleotides to about 2,500 nucleotides.

A probe can further include a detectable label, e.g., a radioactive label, a biotinylated label, a fluorophore (TEXAS RED®, fluorescein isothiocyanate, etc.). The detectable label can be covalently attached directly to the probe oligonucleotide, e.g., located at the probe's 5' end or at the probe's 3' end. A probe including a fluorophore may also further include a quencher, e.g., BLACK HOLE QUENCHER®, IOWA BLACK™, etc.

As used herein, the terms "sequence identity" or "identity" can be used interchangeably and refer to nucleic acid residues in two sequences that are the same when aligned for maximum correspondence over a specified comparison window.

As used herein, the term "percentage of sequence identity" refers to a value determined by comparing two optimally aligned sequences (e.g., nucleic acid sequences or amino acid sequences) over a comparison window, wherein the portion of a sequence in the comparison window may comprise additions or deletions (i.e., gaps) as compared to a reference sequence (that does not comprise additions or deletions) for optimal alignment of the two sequences. A percentage is calculated by determining the number of positions at which an identical nucleic acid or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well known. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al., (1988) *Nucleic Acids Res.* 16:10881-90; Huang et al., (1992) *Comp. Appl. Biosci.* 8:155-65; Pearson et al., (1994) *Methods Mol. Biol.* 24:307-31; Tatiana et al., (1999) *FEMS Microbiol. Lett.* 174:247-50.

The National Center for Biotechnology Information (NCBI) Basic Local Alignment Search Tool (BLAST™; Altschul et al., (1990) *J. Mol. Biol.* 215:403-10) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "operably linked" refers to a nucleic acid placed into a functional relationship with another nucleic acid. Generally, "operably linked" can mean that linked nucleic acids are contiguous. Linking can be accomplished by ligation at convenient restriction sites. If such sites do not exist, synthetic oligonucleotide adaptors or linkers are ligated or annealed to the nucleic acid and used to link the contiguous polynucleotide fragment. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5'-UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) *Genes & Dev.,* 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), a RNA molecule (an RNA-binding protein), and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

Examples of DNA binding proteins include; meganucleases, zinc fingers, CRISPRs, and TALE binding domains that can be "engineered" to bind to a predetermined nucleotide sequence. Typically, the engineered DNA binding proteins (e.g., zinc fingers, CRISPRs, or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALE designs and binding data. See, for example, U.S. Pat. Nos. 6,140, 081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al., (2007)*Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al., (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al., (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al., (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the double-stranded break (DSB) at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) Science 337, pp. 816-821, Jinek et al., (2013), eLife 2:e00471, and David Segal, (2013) eLife 2:e00563). Thus, the CRISPR/Cas system can be engineered to create a DSB at a desired target in a genome, and repair of the DSB can be influenced by the use of repair inhibitors to cause an increase in error prone repair.

In other examples, the DNA binding transgene is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al., (1997) *Nucleic Acids Res.* 25:3379-30 3388; Dujon et al., (1989) *Gene* 82:115-118; Perler et al., (1994) *Nucleic Acids Res.* 22, 11127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al., (2002) *Molec. Cell* 10:895-905; Epinat et al., (2003) *Nucleic Acids Res.* 5 31:2952-2962; Ashworth et al., (2006) *Nature* 441:656-659; Paques et al., (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) *Cell* 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

As used herein, the term "transduce" refers to a process where a virus transfers nucleic acid into a cell.

As used herein, the term "transgene" refers to an exogenous nucleic acid sequence. In one example, a transgene is a gene sequence (e.g., an herbicide-tolerance gene), a gene encoding an industrially or pharmaceutically useful compound, or a gene encoding a desirable agricultural trait. In yet another example, a transgene is a small RNA, such as an antisense nucleic acid sequence, wherein expression of the small RNA sequence inhibits expression of a target nucleic acid sequence. A transgene may contain regulatory sequences operably linked to the transgene (e.g., a promoter, intron, or 3'-UTR). In some embodiments, a nucleic acid of interest is a transgene. However, in other embodiments, a nucleic acid of interest is an endogenous nucleic acid, wherein additional genomic copies of the endogenous nucleic acid are desired, or a nucleic acid that is in the antisense orientation with respect to the sequence of a target nucleic acid in a host organism.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)," "tmRNA" (a.k.a. "10S RNA," Muto et al., (1998) *Trends Biochem Sci.* 23:25-29; and Gillet et al., (2001) *Mol Microbiol.* 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA)," "diced siRNA (d-siRNA)," and aptamers, oligonucleotides and other synthetic nucleic acids that comprise at least one uracil base.

As used herein, the term "vector" refers to a nucleic acid molecule as introduced into a cell, thereby producing a transformed cell. A vector may include nucleic acid sequences that permit it to replicate in the host cell, such as an origin of replication. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome).

As used herein, the terms "cassette," "expression cassette," and "gene expression cassette" refer to a segment of DNA that can be inserted into a nucleic acid or polynucleotide at specific restriction sites or by homologous recombination. A segment of DNA comprises a polynucleotide containing a gene of interest that encodes a small RNA or a polypeptide of interest, and the cassette and restriction sites are designed to ensure insertion of the cassette in the proper reading frame for transcription and translation. In an embodiment, an expression cassette can include a polynucleotide that encodes a small RNA or a polypeptide of interest and having elements in addition to the polynucleotide that facilitate transformation of a particular host cell. In an embodiment, a gene expression cassette may also include elements that allow for enhanced expression of a small RNA or a polynucleotide encoding a polypeptide of interest in a host cell. These elements may include, but are not limited to: a promoter, a minimal promoter, an enhancer, a response element, an intron, a 5' untranslated, a 3' untranslated region sequence, a terminator sequence, a polyadenylation sequence, and the like.

As used herein, the term "heterologous coding sequence" is used to indicate any polynucleotide that codes for, or ultimately codes for, a peptide or protein or its equivalent amino acid sequence, e.g., an enzyme, that is not normally present in the host organism and can be expressed in the host cell under proper conditions. As such, "heterologous coding sequences" may include one or additional copies of coding sequences that are not normally present in the host cell, such that the cell is expressing additional copies of a coding sequence that are not normally present in the cells. The heterologous coding sequences can be RNA or any type thereof, e.g., mRNA, DNA or any type thereof, e.g., cDNA, or a hybrid of RNA/DNA. Examples of coding sequences include, but are not limited to, full-length transcription units that comprise such features as the coding sequence, introns, promoter regions, 5'-UTR, 3'-UTRs and enhancer regions.

"Heterologous coding sequences" also includes the coding portion of the peptide or enzyme, i.e., the cDNA or mRNA sequence, of the peptide or enzyme, as well as the coding portion of the full-length transcriptional unit, i.e., the gene comprising introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences can have a deletion of one or more amino acids, with the deletion being N-terminal, C-terminal, or internal. Truncated forms are envisioned as long as they have the catalytic capability indicated herein.

As used herein, the term "control" refers to a sample used in an analytical procedure for comparison purposes. A control can be "positive" or "negative." For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes plants and plant parts including but not limited to plant cells and plant tissues such as leaves, stems, roots, flowers, pollen, and seeds. A class of plant that can be used in the present invention is generally as broad as the class of higher and lower plants amenable to mutagenesis including angiosperms, gymnosperms, ferns, and multicellular algae. Thus, "plant" includes dicot and monocot plants. Examples of dicotyledonous plants include tobacco, Arabidopsis, soybean, tomato, papaya, canola, sunflower, cotton, alfalfa, potato, grapevine, pigeon pea, pea, Brassica, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants include corn, rice, wheat, sugarcane, barley, rye, sorghum, orchids, bamboo, banana, cattails, lilies, oat, onion, millet, and triticale.

As used herein, the term "plant material" refers to leaves, stems, roots, flowers or flower parts, fruits, pollen, egg cells, zygotes, seeds, cuttings, cell or tissue cultures, or any other part or product of a plant. In an embodiment, plant material includes cotyledon and leaf. In an embodiment, plant material includes root tissues and other plant tissues located underground.

As used herein, the term "selectable marker gene" refers to a gene that is optionally used in plant transformation to, for example, protect plant cells from a selective agent or provide resistance/tolerance to a selective agent. In addition, "selectable marker gene" is meant to encompass reporter genes. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide tolerance including bar or pat (tolerance against glufosinate ammonium or phosphinothricin), acetolactate synthase (ALS, tolerance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the term "detecting" is used in the broadest sense to include both qualitative and quantitative measurements of a specific molecule, for example, measurements of a specific polypeptide.

Unless otherwise specifically explained, all technical and scientific terms used herein have the same meaning as commonly understood by those of ordinary skill in the art that this disclosure belongs. Definitions of common terms in molecular biology can be found in, for example: Lewin, Genes V, Oxford University Press, 1994; Kendrew et al. (eds.), The Encyclopedia of Molecular Biology, Blackwell Science Ltd., 1994; and Meyers (ed.), Molecular Biology and Biotechnology: A Comprehensive Desk Reference, VCH Publishers, Inc., 1995.

Regulatory Elements

Plant promoters used for basic research or biotechnological applications direct the expression of transgene that has been fused at its 3' end (downstream) to robustly express transgenes within plants for metabolic engineering and trait stacking. As a result, there is a need for novel promoters that can drive the expression of multiple genes in transgenic crops. Disclosed, herein is a promoter that can direct the expression of a first gene that has been fused at its 3' end (downstream).

Development of transgenic products is becoming increasingly complex, which requires robustly expressing transgenes and stacking multiple transgenes into a single locus. Traditionally, each transgene requires a unique promoter for expression wherein multiple promoters are required to express different transgenes within one gene stack. With an increasing size of gene stacks, this frequently leads to repeated use of the same promoter to obtain similar levels of expression patterns of different transgenes for expression of a single polygenic trait. Multi-gene constructs driven by the same promoter are known to cause gene silencing resulting in less efficacious transgenic products in the field. Excess of transcription factor (TF)-binding sites due to promoter repetition can cause depletion of endogenous TFs leading to transcriptional inactivation. The silencing of transgenes will likely undesirably affect performance of a transgenic plant produced to express transgenes. Repetitive sequences within a transgene may lead to gene intra locus homologous recombination resulting in polynucleotide rearrangements.

Tissue specific (i.e., tissue-preferred) or organ specific promoters drive gene expression in a certain tissue such as in the kernel, root, leaf, or tapetum of the plant. Tissue and developmental stage specific promoters derive the expression of genes, which are expressed in particular tissues or at particular time periods during plant development. Tissue specific promoters are required for certain applications in the transgenic plant industry and are desirable as they permit specific expression of heterologous genes in a tissue and/or developmental stage selective manner, indicating expression of the heterologous gene differentially at a various organs, tissues and/or times, but not in other. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Another application is the desirability of using tissue specific promoters, e.g., such that would confine the expression of the transgenes encoding an agronomic trait in developing xylem. One particular problem remaining in the identification of tissue specific promoters is how to identify the potentially most important genes and their corresponding promoters, and to relate these to specific developmental properties of the cell. Another problem is to clone all relevant cis-acting transcriptional control elements so that the cloned DNA fragment drives transcription in the wanted specific expression pattern. Given that such control elements are located distally from the translation initiation or start site, the size of the polynucleotide that is selected to comprise the promoter is of importance for providing the level of expression and the expression patterns of the promoter polynucleotide sequence. A particular problem is to identify tissue-specific promoters, related to specific cell types, developmental stages and/or functions in the plant that are not expressed in other plant tissues.

Provided are methods and constructs using *Zea mays* chlorophyll a/b binding gene promoter regulatory elements to express transgenes in plant. In an embodiment, a promoter can be a full length *Zea mays* chlorophyll a/b binding gene promoter of:

```
                                              (SEQ ID NO: 1)
GCACAAAATACATAAAACTAGATTAGAAAAGGAAGAGAATACGCCAAATT

GCAGCTTAATCAATTAGACGATTTAGTCCTGTTTTTACGAAACAATTGTT

TAAGATAACATTAGGACATGTACAATATGTGTCTTTGGATGTGTTTAAGG

AGTAAATGTAAAAAAATAGATACGTCTCTTAACGAAGTCATTGTGTCTT

GGCTCTATGCTCGAGACGGAGAAATAGCTAATTGATTAATTTAATTTATT

GAATGTTCTTATTGGTGTAATGAATATAGTAAGGCACTGGCCTTATACTT

GGAGTTTGGCATGTCTTATGCTATGTTGCAAACAGGCCCGGTCTTGACAT

TTCGGGGGCCCTAAGAGAAAATTTATATAGAGGTCCTATACGAAAATTTG

AGTCTGTTATTTTTTCAACTTTTAAATAATATATGAAAAATAAAAAATTG

ATGATTTACATAATTTTATTCAAAATGATATGACTGGAAATATTGTTACA

GTATTTTATGAGTCGTAAAATTATATAAATTATGTAATATACATTTGTTT

TGACTTTTGAGAGAGTATTTTTACTTTTAATTTGTCAAACTAGCCTAAAC

CTTAAAATACACAGTAAACCAAATCTAAATACATTAGATCAAATTTTCTG

AAAATAAAGTTCAGCAAACTAAACTAGGATTAATCAATGTAGGTTATTAG

GGTCGACCCTTCGGTAGGCTAGAATTAAGCAACGCGATAGGCACAGGTGT

ACAACACCTTTCGTCCTTCCCACGTCAATTTTAGGGCCTGTTTGGTTCAC

GGCTAATTATGCCACACTTTGCCTAAGGTTAGTCGTCCGAATTGAAGAAC

TAACCTTATGCAGAAAAGTTAGGCAAAGTATGGCAAGTTAGGTAGTAAAC

CAAACAGGCCAAAGTATTTGTCATCAAGCAGACGGTTGCGCGACCTCAAA

GAGATGATTGCTAGAAAATAAAGAGACGCAACAAAAGAATGAAAATATAG

ATTTATCTATAACTTATATGCATTTGATATAAGATAGATAAATGGGAGCC

CTACGAACCTTGAGGCTCTGAGCAGTCGCATATCCTGCACACCCTTGGCG

CCGGCCCTGGTTGCAAATATGCAATTGTGTCCTTATCCGCGACTGGTCAC

GAGGCTAGGATTGATCGAAAGCTGCCGATGAGAAATGGCAAGGGCGGCAT

GCTGTGGCCTTTTTTTTACGGTCTGTCAGGACAACTGAAAAGTTACAAAT

TTATAGTGGTTGTAAACAGCAACACGTTAAAAAGTCGATTATCAGTTTCA

CAGAAAGAGGTCGTTAAAACCGCCAGCAAGCTTGTTTCACTATCAGTCTG

TCGCTAAGACAATCTCTTTCACCAAAAATACAATTTGCTTTCTTGCCGTT

GCTTCAAGTGAAAATCTTAATGTTTTAAATTAAAATATGTGGCTCTACGT

AGGAAAAAATAATTCAATCGAGTCTCATTTCATAAAAAAATTTGGTCAA

AAAATTATACACCATCTCGCTCAAGTGACTCAAATATACTAAACGGTACT

GAGCTGTCTTATAATATAAATTTGATTTACTGTTAGAATATGATGTTTTA

TGAGTGCACTAAATTCTATAAAATATATTTATTTTTAAATTATAAGATAT

TTTTATAGGTCTGCTCTTAGAGAGAGCTAAAAAAGAGAGAGGCTGTCTGA

AGAAAAATCCATAACCAACGCAAAATCCCGGGCGCCCAATCAGCCTTCTC

CGCGGAGATTCCTAGCCTCAGCCAGAGCTACCTCATCTGCGTGAGGCTCC

GGTGGCGCCAAGTGTTCCGGCATCCCGGACGCACCAATGGCATCCGAGCA

ACAGATCTTTTCTGCAACAACGCTTCGCGTCGCGGCGGTGTTTCCCTCCA

TCTGCTCTGCTCTTTAAATACCTCCGTCGTCTCCTCGTCTCCACAGCATC

TCAAGTCTTCACACTCCTCGCCATCACATAAAACCAGTGCAAGCAGAAGC

AGCGCA
```

In an embodiment, a promoter can be a full length *Zea mays* chlorophyll a/b binding gene upstream-promoter of:

```
                                              (SEQ ID NO: 2)
GCACAAAATACATAAAACTAGATTAGAAAAGGAAGAGAATACGCCAAATT

GCAGCTTAATCAATTAGACGATTTAGTCCTGTTTTTACGAAACAATTGTT

TAAGATAACATTAGGACATGTACAATATGTGTCTTTGGATGTGTTTAAGG
```

-continued

AGTAAATGTAAAAAAAATAGATACGTCTCTTAACGAAGTCATTGTGTCTT

GGCTCTATGCTCGAGACGGAGAAATAGCTAATTGATTAATTTAATTTATT

GAATGTTCTTATTGGTGTAATGAATATAGTAAGGCACTGGCCTTATACTT

GGAGTTTGGCATGTCTTATGCTATGTTGCAAACAGGCCCGGTCTTGACAT

TTCGGGGCCCTAAGAGAAAATTTATATAGAGGTCCTATACGAAAATTTG

AGTCTGTTATTTTTCAACTTTTAAATAATATATGAAAAATAAAAATTG

ATGATTTACATAATTTTATTCAAAATGATATGACTGGAAATATTGTTACA

GTATTTTATGAGTCGTAAAATTATATAAATTATGTAATATACATTTGTTT

TGACTTTTGAGAGAGTATTTTTACTTTTAATTTGTCAAACTAGCCTAAAC

CTTAAAATACACAGTAAACCAAATCTAAATACATTAGATCAAATTTTCTG

AAAATAAAGTTCAGCAAACTAAACTAGGATTAATCAATGTAGGTTATTAG

GGTCGACCCTTCGGTAGGCTAGAATTAAGCAACGCGATAGGCACAGGTGT

ACAACACCTTTCGTCCTTCCCACGTCAATTTTAGGGCCTGTTTGGTTCAC

GGCTAATTATGCCACACTTTGCCTAAGGTTAGTCGTCCGAATTGAAGAAC

TAACCTTATGCAGAAAAGTTAGGCAAAGTATGGCAAGTTAGGTAGTAAAC

CAAACAGGCCAAAGTATTTGTCATCAAGCAGACGGTTGCGCGACCTCAAA

GAGATGATTGCTAGAAAATAAAGAGACGCAACAAAAGAATGAAAATATAG

ATTTATCTATAACTTATATGCATTTGATATAAGATAGATAAATGGGAGCC

CTACGAACCTTGAGGCTCTGAGCAGTCGCATATCCTGCACACCCTTGGCG

CCGGCCCTGGTTGCAAATATGCAATTGTGTCCTTATCCGCGACTGGTCAC

GAGGCTAGGATTGATCGAAAGCTGCCGATGAGAAATGGCAAGGGCGGCAT

GCTGTGGCCTTTTTTTTACGGTCTGTCAGGACAACTGAAAAGTTACAAAT

TTATAGTGGTTGTAAACAGCAACACGTTAAAAAGTCGATTATCAGTTTCA

CAGAAAGAGGTCGTTAAAACCGCCAGCAAGCTTGTTTCACTATCAGTCTG

TCGCTAAGACAATCTCTTTCACCAAAAATACAATTTGCTTTCTTGCCGTT

GCTTCAAGTGAAAATCTTAATGTTTTAAATTAAAATATGTGGCTCTACGT

AGGAAAAAATAATTCAATCGAGTCTCATTTCATAAAAAAAATTTGGTCAA

AAAATTATACACCATCTCGCTCAAGTGACTCAAATATACTAAACGGTACT

GAGCTGTCTTATAATATAAATTTGATTTACTGTTAGAATATGATGTTTTA

TGAGTGCACTAAATTCTATAAAATATATTTATTTTTAAATTATAAGATAT

TTTTATAGGTCTGCTCTTAGAGAGAGCTAAAAAAGAGAGAGGCTGTCTGA

AGAAAAATCCATAACCAACGCAAATCCCGGGCGCCCAATCAGCCTTCTC

CGCGGAGATTCCTAGCCTCAGCCAGAGCTACCTCATCTGCGTGAGGCTCC

GGTGGCGCCAAGTGTTCCGGCATCCCGGACGCACCAATGGCATCCGAGCA

ACAGATCTTTTCTGCAACAACGCTTCGCGTCGCGGCG

In an embodiment, a promoter can be a modified *Zea mays* chlorophyll a/b binding gene promoter of:

(SEQ ID NO: 3)
GCACAAAATACATAAAACTAGATTAGAAAAGGAAGAGAATACGCCAAATT

GCAGCTTAATCAATTAGACGATTTAGTCCTGTTTTTACGAAACAATTGTT

TAAGATAACATGGCCTTATACTTGGAGTTTGGCATGTCTTATGCTATGTT

GCAAACAGGCCCGGTCTTGACATTTCGGGGCCCTAAGAGAAAATTTATA

TAGAGGTCCTATACGAAAATTTGAGTCTGTTATTTTTTCAACTTTTAAAT

AATATATGAAAATAAAAAATTGATGATTTACATAATTTTATTCAAAATG

ATATGACTGGAAATATTGTTACAGTATTTTATGAGTCGTAAAATTATATA

AATTATGTAATATACATTTGTTTTGACTTTTGAGAGAGTATTTTTACTTT

TAATTTGTCAAACTAGCCTAAACCTTAAAATACACAGTAAACCAAATCTA

AATACATTAGATCAAATTTTCTGAAAATAAAGTTCAGCAAACTAAACTAG

GATTAATCAATGTAGGTTATTAGGGTCGACCCTTCGGTAGGCTAGAATTA

AGCAACGCGATAGGCACAGGTGTACAACACCTTTCGTCCTTCCCACGTCA

ATAAAGTATTTGTCATCAAGCAGACGGTTGCGCGACCTCAAAGAGATGAT

TGCTAGAAAATAAAGAGACGCAACAAAAGAATGAAAATATAGATTTATCT

ATAACTTATATGCATTTGATATAAGATAGATAAATGGGAGCCCTACGAAC

CTTGAGGCTCTGAGCAGTCGCATATCCTGCACACCCTTGGCGCCGGCCCT

GGTTGCAAATATGCAATTGTGTCCTTATCCGCGACTGGTCACGAGGCTAG

GATTGATCGAAAGCTGCCGATGAGAAATGGCAAGGGCGGCATGCTGTGGC

CTTTTTTTTACGGTCTGTCAGGACAACTGAAAAGTTACAAATTTATAGTG

GTTGTAAACAGCAACACGTTAAAAAGTCGATTATCAGTTTCACAGAAAGA

GGTCGTTAAAACCGCCAGCAAGCTTGTTTCACTATCAGTCTGTCGCTAAG

ACAATCTCTTTCACCAAAAATACAATTTGCTTTCTTGCCGTTGCTTCAAG

TGAAAATCTGAGCTAAAAAAGAGAGAGGCTGTCTGAAGAAAAATCCATAA

CCAACGCAAATCCCGGGCGCCCAATCAGCCTTCTCCGCGGAGATTCCTA

GCCTCAGCCAGAGCTACCTCATCTGCGTGAGGCTCCGGTGGCGCCAAGTG

TTCCGGCATCCCGGACGCACCAATGGCATCCGAGCAACAGATCTTTTCTG

CAACAACGCTTCGCGTCGCGGCGGTGTTTCCCTCCATCTGCTCTGCTCTT

TAAATACCTCCGTCGTCTCCTCGTCTCCACAGCATCTCAAGTCTTCACAC

TCCTCGCCATCACATAAAACCAGTGCAAGCAGAAGCAGCGCA

In an embodiment, a promoter can be a modified *Zea mays* chlorophyll a/b binding gene upstream-promoter of:

(SEQ ID NO: 4)
GCACAAAATACATAAAACTAGATTAGAAAAGGAAGAGAATACGCCAAATT

GCAGCTTAATCAATTAGACGATTTAGTCCTGTTTTTACGAAACAATTGTT

TAAGATAACATGGCCTTATACTTGGAGTTTGGCATGTCTTATGCTATGTT

GCAAACAGGCCCGGTCTTGACATTTCGGGGCCCTAAGAGAAAATTTATA

TAGAGGTCCTATACGAAAATTTGAGTCTGTTATTTTTTCAACTTTTAAAT

AATATATGAAAATAAAAAATTGATGATTTACATAATTTTATTCAAAATG

ATATGACTGGAAATATTGTTACAGTATTTTATGAGTCGTAAAATTATATA

AATTATGTAATATACATTTGTTTTGACTTTTGAGAGAGTATTTTTACTTT

TAATTTGTCAAACTAGCCTAAACCTTAAAATACACAGTAAACCAAATCTA

AATACATTAGATCAAATTTTCTGAAAATAAAGTTCAGCAAACTAAACTAG

GATTAATCAATGTAGGTTATTAGGGTCGACCCTTCGGTAGGCTAGAATTA

```
AGCAACGCGATAGGCACAGGTGTACAACACCTTTCGTCCTTCCCACGTCA

ATAAAGTATTTGTCATCAAGCAGACGGTTGCGCGACCTCAAAGAGATGAT

TGCTAGAAAATAAAGAGACGCAACAAAAGAATGAAAATATAGATTTATCT

ATAACTTATATGCATTTGATATAAGATAGATAAATGGGAGCCCTACGAAC

CTTGAGGCTCTGAGCAGTCGCATATCCTGCACACCCTTGGCGCCGGCCCT

GGTTGCAAATATGCAATTGTGTCCTTATCCGCGACTGGTCACGAGGCTAG

GATTGATCGAAAGCTGCCGATGAGAAATGGCAAGGGCGGCATGCTGTGGC

CTTTTTTTTACGGTCTGTCAGGACAACTGAAAAGTTACAAATTTATAGTG

GTTGTAAACAGCAACACGTTAAAAAGTCGATTATCAGTTTCACAGAAAGA

GGTCGTTAAAACCGCCAGCAAGCTTGTTTCACTATCAGTCTGTCGCTAAG

ACAATCTCTTTCACCAAAAATACAATTTGCTTTCTTGCCGTTGCTTCAAG

TGAAAATCTGAGCTAAAAAAGAGAGAGGCTGTCTGAAGAAAAATCCATAA

CCAACGCAAAATCCCGGGCGCCCAATCAGCCTTCTCCGCGGAGATTCCTA

GCCTCAGCCAGAGCTACCTCATCTGCGTGAGGCTCCGGTGGCGCCAAGTG

TTCCGGCATCCCGGACGCACCAATGGCATCCGAGCAACAGATCTTTTCTG

CAACAACGCTTCGCGTCGCGGCG
```

In an embodiment, a gene expression cassette comprises a promoter. In an embodiment, a promoter can be a *Zea mays* chlorophyll a/b binding gene promoter of the subject disclosure. In an embodiment, a gene expression cassette comprises a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:4. In an embodiment, a gene expression cassette comprises a *Zea mays* chlorophyll a/b binding gene promoter that is operably linked to a transgene. In an embodiment, a gene expression cassette comprising the *Zea mays* chlorophyll a/b binding gene promoter may drive expression of two or more transgenes. In an illustrative embodiment, a gene expression cassette comprises a *Zea mays* chlorophyll a/b binding gene promoter that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

Transgene expression may also be regulated by an intron region located downstream of the promoter sequence. Both a promoter and an intron can regulate transgene expression. While a promoter is necessary to drive transcription, the presence of an intron can increase expression levels resulting in mRNA transcript for translation and protein synthesis. An intron gene region aids stable expression of a transgene.

In an embodiment, a gene expression cassette comprises an intron. In an embodiment, a gene expression cassette comprises an intron from *Zea mays* chlorophyll a/b binding gene. In an embodiment, the intron can be a *Zea mays* chlorophyll a/b binding gene intron (1) of:

```
                                        (SEQ ID NO: 5)
GTGTTTCCCTCCATCTGCTCTGCTCTTTAAATACCTCCGTCGTCTCCTCG

TCTCCACAG
```

In an embodiment, an intron can be the *Zea mays* chlorophyll a/b binding gene intron (2) of:

```
                                        (SEQ ID NO: 6)
GTGGAGGCGCCACCGCCCACCGGCCACCGCTGCGGATATCTAG
```

In an embodiment, a gene expression cassette comprises an intron, wherein the intron is at least 80%, 85%, 90%, 91%, 92%, 93%, 94%, 95%, 96%, 97%, 98%, 99%, 99.5%, 99.8%, or 100% identical to SEQ ID NO:5 or SEQ ID NO:6. In an embodiment, a gene expression cassette comprises an intron from a *Zea mays* chlorophyll a/b binding gene that is operably linked to a promoter, wherein the promoter is a *Zea mays* gene promoter, or a promoter that originates from a plant (e.g., *Zea mays* chlorophyll a/b binding gene promoter or *Zea mays* ubiquitin 1 promoter), a virus (e.g., Cassava vein mosaic virus promoter), or a bacteria (e.g., *Agrobacterium tumefaciens* delta mas). In an illustrative embodiment, a gene expression cassette comprises an intron from a *Zea mays* chlorophyll a/b binding gene that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

Transgene expression may also be regulated by a 3'-untranslated gene region (i.e., 3'-UTR) located downstream of the gene's coding sequence. Both a promoter and a 3'-UTR can regulate transgene expression. While a promoter is necessary to drive transcription, a 3'-UTR gene region can terminate transcription and initiate polyadenylation of a resulting mRNA transcript for translation and protein synthesis. A 3'-UTR gene region aids stable expression of a transgene. In an embodiment, a 3'-UTR can be a full length *Zea mays* chlorophyll a/b binding gene 3'-UTR of:

```
                                        (SEQ ID NO: 7)
GGGGGTGGAGGCGCCACCGCCCACCGGCCACCGCTGCGGATATCTAGGTG

TTCGGATGCACGTGAGCGCGCACTGGTTCCAGTTTGTACCATGATGTAAA

TTACTTACCGTACCAGGGTTCAATCGGCAAGGAAGAATTGTTGTGTTCAC

TGTCTTGGGCAGTCTCTTGGTCCAATATGAATCAACTTACACAGCATCTC

CAAAAACTTCTAAAATTACTAGCTGAATGCCCGTGCGTTGCAACGGGAAT

ATATAATACCAGTATACTACGATAACTTATATACAAAATGTATGTTATAT

CGTTATGAGAAAATGTTTCATAACCAATTTATGATTCTGGTCATACATAA

ATTTTGTTATTTATAGTCTATCTGTTTCACCACTACATTGCAACCATCAG

TATCATGCAGACTTCGATATATGTTACGATTTGTATGGTCTCATTATTGG

AGAGCACGTTCCACACATACCGGAAGAAATTTTCTCGTACATCGTTAGTC

ATCAGACACGTACCACCATACACTTTTGCTTAAACAAAAATGCAAGTGTG

TGTTTGCGAAGAGAATTAAAGGCAAGTCGACACAAAAGCTACCCCAACGG

TGGCGAGGATGACGAACTGGTCATTTTTGTCGGTCCTCCCCTGCGTCACC

TCTGGCGCCAAGATGACGCCATAGTCCTCGATATAGTAATCGTCGAACGC

GCGCGACATACCGAGTACTGATGACTCTTGGCTGGGCTGTAAAACGAAGT

GCACCCCGGGCTCATCAGCAAGGTAGTACCCCTGGTCGTTGCACTACCGG

ATGCGCTACTACTCTACATGCATCGTGTTCGAGGATACTCATACAACGTC
```

-continued

```
AGCAACGGCTATCGTCTCAGTGCACAAGAATTCATGCCTAGTCAGTAGCG

ACTTACGTGGCTGGTTGGGCTTCAGGTGAACGATGAGCTGGACAACGTGA

TGGCGTCGTCGTCGAATGCAGTGCCCAGAACAACCCGAAAGTCGCCGACG
```

In an embodiment, a 3'-UTR can be a modified *Zea mays* chlorophyll a/b binding gene 3'-UTR:

```
                                         (SEQ ID NO: 8)
GGGGGTGGAGGCGCCACCGCCCACCGGCCACCGCTGCGGATATCTAGGTG

TTCGGATGCACGTGAGCGCGCACTGGTTCCAGTTTGTACCATGATGTAAA

TTACTTACCGTACCAGGGTTCAATCGGCAAGGAAGAATTGTTGTGTTCAC

TGTCTTGGGCAGTCTCTTGGTCCAATATGAATCAACTTACACAGCATCTC

CAAAAACTTCTAAAATTACTAGCTGAATGCCCGTGCGTTGCAACGGGAAT

ATATAATACCAGTATACTACGATAACTTATATACAAAATGTATGTTATAT

CGTTATGAGAAAATGTTTCATAACCAATTTATGATTCTGGTCATACATAA

ATTTTGTTATTTATAGTCTATCTGTTTCACCACTACATTGCAACCATCAG
```

In an embodiment, a gene expression cassette comprises a 3'-UTR. In an embodiment, a 3'-UTR can be a *Zea mays* chlorophyll a/b binding gene 3'-UTR. In an embodiment, a gene expression cassette comprises a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:7 or SEQ ID NO:8. In an embodiment, a gene expression cassette comprises a *Zea mays* chlorophyll a/b binding gene 3'-UTR that is operably linked to a transgene. In an illustrative embodiment, a gene expression cassette comprises a 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a gene expression cassette comprises a promoter, intron, and a 3'-UTR purified from the *Zea mays* chlorophyll a/b binding gene. In an embodiment, a gene expression cassette comprises: a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:4; b) an intron, wherein the intron is at least 80%, 85%, 90%, 91%, 92%, 93%, 94%, 95%, 96%, 97%, 98%, 99%, 99.5%, 99.8%, or 100% identical to SEQ ID NO:5, SEQ ID NO:6; and/or, c) a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:7 or SEQ ID NO:8.

For example, a gene expression cassette may include both a promoter and a 3'-UTR wherein the promoter is a polynucleotide of SEQ ID NO:1, and the 3'-UTR is a polynucleotide of SEQ ID NO:7. In another embodiment, a gene expression cassette may include both a promoter and a 3'-UTR wherein the promoter is a polynucleotide of SEQ ID NO:1, and the 3'-UTR is a polynucleotide of SEQ ID NO:8. In a subsequent embodiment, a gene expression cassette may include both a promoter and a 3'-UTR wherein the promoter is a polynucleotide of SEQ ID NO:2, and the 3'-UTR is a polynucleotide of SEQ ID NO:7. In yet another embodiment, a gene expression cassette may include both a promoter and a 3'-UTR wherein the promoter is a polynucleotide of SEQ ID NO:2, and the 3'-UTR is a polynucleotide of SEQ ID NO:8.

In a further embodiment, a gene expression cassette may include both a promoter and a 3'-UTR wherein the promoter is a polynucleotide of SEQ ID NO:3, and the 3'-UTR is a polynucleotide of SEQ ID NO:7. In yet another embodiment, a gene expression cassette may include both a promoter and a 3'-UTR wherein the promoter is a polynucleotide of SEQ ID NO:3, and the 3'-UTR is a polynucleotide of SEQ ID NO:8. In an embodiment, a gene expression cassette may include both a promoter and a 3'-UTR wherein the promoter is a polynucleotide of SEQ ID NO:4, and the 3'-UTR is a polynucleotide of SEQ ID NO:7. In yet another embodiment, a gene expression cassette may include both a promoter and a 3'-UTR wherein the promoter is a polynucleotide of SEQ ID NO:4, and the 3'-UTR is a polynucleotide of SEQ ID NO:8.

In another embodiment, the gene expression cassette may include a promoter, intron, and a 3'-UTR, wherein the promoter is a polynucleotide of SEQ ID NO:1, the intron is a polynucleotide of SEQ ID NO:5, and the 3'-UTR is a polynucleotide of SEQ ID NO:7. In a further embodiment, the gene expression cassette may include a promoter, intron, and a 3'-UTR, wherein the promoter is a polynucleotide of SEQ ID NO:1, the intron is a polynucleotide of SEQ ID NO:5, and the 3'-UTR is a polynucleotide of SEQ ID NO:8. In an additional embodiment, the gene expression cassette may include a promoter, intron, and a 3'-UTR, wherein the promoter is a polynucleotide of SEQ ID NO:3, the intron is a polynucleotide of SEQ ID NO:5, and the 3'-UTR is a polynucleotide of SEQ ID NO:7. In a further embodiment, the gene expression cassette may include a promoter, intron, and a 3'-UTR, wherein the promoter is a polynucleotide of SEQ ID NO:3, the intron is a polynucleotide of SEQ ID NO:5, and the 3'-UTR is a polynucleotide of SEQ ID NO:8.

In another embodiment, the gene expression cassette may include a promoter, intron, and a 3'-UTR, wherein the promoter is a polynucleotide of SEQ ID NO:2, the intron is a polynucleotide of SEQ ID NO:5, and the 3'-UTR is a polynucleotide of SEQ ID NO:7. In a further embodiment, the gene expression cassette may include a promoter, intron, and a 3'-UTR, wherein the promoter is a polynucleotide of SEQ ID NO:2, the intron is a polynucleotide of SEQ ID NO:5, and the 3'-UTR is a polynucleotide of SEQ ID NO:8. In an additional embodiment, the gene expression cassette may include a promoter, intron, and a 3'-UTR, wherein the promoter is a polynucleotide of SEQ ID NO:4, the intron is a polynucleotide of SEQ ID NO:5, and the 3'-UTR is a polynucleotide of SEQ ID NO:7. In a further embodiment, the gene expression cassette may include a promoter, intron, and a 3'-UTR, wherein the promoter is a polynucleotide of SEQ ID NO:4, the intron is a polynucleotide of SEQ ID NO:5, and the 3'-UTR is a polynucleotide of SEQ ID NO:8.

In an embodiment, a 5'-UTR can be a modified *Zea mays* chlorophyll a/b binding gene 5'-UTR:

```
                                        (SEQ ID NO: 19)
CATCTCAAGTCTTCACACTCCTCGCCATCACATAAAACCAGTGCAAGCAG

AAGCAGCGCA
```

In an embodiment, a nucleic acid construct is provided comprising a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:19. In an embodiment, a gene expression cassette comprises a 5'-UTR. In an embodiment, a 5'-UTR can be a *Zea mays* chlorophyll a/b binding gene 5'-UTR. In an embodiment, a gene expression cassette comprises a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:19. In an embodiment, a gene expression cassette comprises a *Zea mays* chlorophyll a/b binding gene 5'-UTR that is operably linked to a transgene. In an illustrative embodiment, a gene expression cassette comprises a 5'-UTR that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

In an embodiment, a gene expression cassette comprises a promoter, intron, and a 5'-UTR purified from the *Zea mays* chlorophyll a/b binding gene. In an embodiment, a gene expression cassette comprises: a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:4; b) an intron, wherein the intron is at least 80%, 85%, 90%, 91%, 92%, 93%, 94%, 95%, 96%, 97%, 98%, 99%, 99.5%, 99.8%, or 100% identical to SEQ ID NO:5, SEQ ID NO:6; and/or, c) a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:19.

For example, a gene expression cassette may include both a promoter and a 5'-UTR wherein the promoter is a polynucleotide of SEQ ID NO:1 and the 5'-UTR is a polynucleotide of SEQ ID NO:19. In a subsequent embodiment, a gene expression cassette may include both a promoter and a 5'-UTR wherein the promoter is a polynucleotide of SEQ ID NO:2 and the 5'-UTR is a polynucleotide of SEQ ID NO:19.

In a further embodiment, a gene expression cassette may include both a promoter and a 5'-UTR wherein the promoter is a polynucleotide of SEQ ID NO:3 and the 5'-UTR is a polynucleotide of SEQ ID NO:19. In yet another embodiment, a gene expression cassette may include both a promoter and a 5'-UTR wherein the promoter is a polynucleotide of SEQ ID NO:4 and the 5'-UTR is a polynucleotide of SEQ ID NO:19.

In another embodiment, the gene expression cassette may include a promoter, intron, and a 5'-UTR, wherein the promoter is a polynucleotide of SEQ ID NO:2, the intron is a polynucleotide of SEQ ID NO:5, and the 5'-UTR is a polynucleotide of SEQ ID NO:19. In a further embodiment, the gene expression cassette may include a promoter, intron, and a 5'-UTR, wherein the promoter is a polynucleotide of SEQ ID NO:4, the intron is a polynucleotide of SEQ ID NO:5, and the 5'-UTR is a polynucleotide of SEQ ID NO:19.

A promoter, an intron, a 3'-UTR, and/or 5'-UTR can be operably linked to different transgenes within a gene expression cassette when a gene expression cassette includes one or more transgenes. In an illustrative embodiment, a gene expression cassette comprises a *Zea mays* gene promoter (SEQ ID NO:1, SEQ ID NO:2, SEQ ID NO:3, or SEQ ID NO:4) that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* gene promoter (SEQ ID NO:1, SEQ ID NO:2, SEQ ID NO:3, or SEQ ID NO:4), an intron (SEQ ID NO:5 or SEQ ID NO:6), and a 5'-UTR (SEQ ID NO:19) that are operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* gene 3'-UTR (SEQ ID NO:7 or SEQ ID NO:8) that is operably linked to a transgene, wherein the transgene can be an insecticidal resistance transgene, a herbicide tolerance transgene, a nitrogen use efficiency transgene, a water us efficiency transgene, a nutritional quality transgene, a DNA binding transgene, a selectable marker transgene, or combinations thereof. In another illustrative embodiment, a gene expression cassette comprises a *Zea mays* gene 5'-UTR (SEQ ID NO:19) that is operably linked to a transgene, wherein the transgene can be an insecticidal resistance transgene, a herbicide tolerance transgene, a nitrogen use efficiency transgene, a water us efficiency transgene, a nutritional quality transgene, a DNA binding transgene, a selectable marker transgene, or combinations thereof.

In an embodiment, a vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in transformation or gene targeting such as a donor DNA.

In an embodiment, a cell or plant comprises a gene expression cassette as disclosed herein. In an embodiment, a cell or plant comprises a vector comprising a gene expression cassette as disclosed herein. In an embodiment, a vector can be a plasmid, a cosmid, a bacterial artificial chromosome (BAC), a bacteriophage, or a virus. Thereby, a cell or plant comprising a gene expression cassette as disclosed herein is a transgenic cell or transgenic plant, respectively. In an embodiment, a transgenic plant can be a monocotyledonous plant. In an embodiment, a transgenic monocotyledonous plant can be, but is not limited to maize, wheat, rice, sorghum, oats, rye, bananas, sugar cane, and millet. In an embodiment, a transgenic plant can be a dicotyledonous plant. In an embodiment, a transgenic dicotyledonous plant can be, but is not limited to soybean, cotton, sunflower, and canola. An embodiment also includes a transgenic seed from a transgenic plant as disclosed herein.

In an embodiment, a gene expression cassette includes two or more transgenes. The two or more transgenes may be operably linked to a *Zea mays* chlorophyll a/b binding gene promoter, intron, or 3'-UTR as disclosed herein. In an embodiment, a gene expression cassette includes one or more transgenes. In an embodiment with one or more transgenes, at least one transgene is operably linked to a *Zea mays* chlorophyll a/b binding gene promoter, intron, or 3'-UTR or the subject disclosure.

Selectable Markers

Various selectable markers also described as reporter genes can be incorporated into a chosen expression vector to allow for identification and selection of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector, e g., precipitated protein that mediates phosphinothricin resistance, or visual observation of other proteins such as reporter genes encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like (See Sambrook, et al., Molecular Cloning: A Laboratory Manual, Third Edition, Cold Spring Harbor Press, N. Y., 2001, the content is incorporated herein by reference in its entirety).

Selectable marker genes are utilized for selection of transformed cells or tissues. Selectable marker genes include genes encoding antibiotic resistance, such as those encoding neomycin phosphotransferase II (NEO) and hygromycin phosphotransferase (HPT) as well as genes conferring tolerance to herbicidal compounds. Herbicide tolerance genes generally code for a modified target protein insensitive to the herbicide or for an enzyme that degrades or detoxifies the herbicide in the plant before it can act. For example, tolerance to glyphosate has been obtained by using genes coding for mutant target enzymes, 5-enolpyruvylshikimate-3-phosphate synthase (EPSPS). Genes and mutants for EPSPS are well known, and further described below. Tolerance to glufosinate ammonium, bromoxynil, and 2,4-dichlorophenoxyacetate (2,4-D) have been obtained by using bacterial genes encoding pat or DSM-2, a nitrilase, an aad-1 or an aad-12 gene, which detoxifies the respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate tolerance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar genes from Streptomyces species, including Streptomyces hygroscopicus and Streptomyces viridichromogenes, and pyridinoxy or phenoxy proprionic acids and cyclohexones (ACCase inhibitor-encoding genes). Exemplary genes conferring resistance to cyclohexanediones and/or aryloxyphenoxypropanoic acid (including Haloxyfop, Diclofop, Fenoxyprop, Fluazifop, Quizalofop) include genes of acetyl coenzyme A carboxylase (ACCase)-Acc1-S1, Acc1-S2, and Acc1-S3. In an embodiment, herbicides can inhibit photosynthesis, including triazine (psbA and 1s+ genes) or benzonitrile (nitrilase gene).

In an embodiment, selectable marker genes include, but are not limited to genes encoding: neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA).

An embodiment also includes genes encoding resistance to: chloramphenicol; methotrexate; hygromycin; spectinomycin; bromoxynil; glyphosate; and phosphinothricin.

The above list of selectable marker genes is not meant to be limiting. Any reporter or selectable marker gene are encompassed by the present invention.

Selectable marker genes are synthesized for optimal expression in a plant. For example, in an embodiment, a coding sequence of a gene has been modified by codon optimization to enhance expression in plants. A selectable marker gene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a selectable marker gene is designed to be expressed in plants at a higher level resulting in higher transformation efficiency. Methods for plant optimization of genes are well known. Guidance regarding the optimization and manufacture of synthetic polynucleotide sequences can be found in, for example, WO2013016546, WO2011146524, WO1997013402, U.S. Pat. No. 6,166,302, and U.S. Pat. No. 5,380,831, herein incorporated by reference.

Transgenes

The disclosed methods and compositions can be used to express polynucleotide gene sequences within the plant genome. Accordingly, expression of genes encoding herbicide tolerance, insect resistance, nutrients, antibiotics, or therapeutic molecules can be driven by a plant promoter.

In one embodiment the Zea mays chlorophyll a/b binding gene regulatory element of the subject disclosure is combined or operably linked with gene encoding polynucleotide sequences that provide resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical, or other uses. The transgenes can be "stacked" with two or more nucleic acid sequences of interest within a plant genome. Stacking can be accomplished, for example, via conventional plant breeding using two or more events, transformation of a plant with a construct which contains the sequences of interest, re-transformation of a transgenic plant, or addition of new traits through targeted integration via homologous recombination.

Such polynucleotide sequences of interest include, but are not limited to, those examples provided below:

1. Genes or Coding Sequence (e.g., iRNA) that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to Cladosporium fulvum (Jones et al., 1994 Science 266:789), tomato Pto gene, which encodes a protein kinase, for resistance to Pseudomonas syringae pv. tomato (Martin et al., 1993 Science 262:1432), and Arabidopsis RSSP2 gene for resistance to Pseudomonas syringae (Mindrinos et al., 1994 Cell 78:1089).

(B) A Bacillus thuringiensis protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al., (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995, and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an a-amylase inhibitor (Sumitani et al., 1993 Biosci. Biotech. Biochem. 57:1243).

(F) An insect-specific hormone or pheromone such as an ecdysteroid and juvenile hormone, a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyubiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 Plant Sci. 89:43) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al., (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al., (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al., (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992 Bio/Technology 10:1436). The cloning and characterization of a gene which encodes a bean endopolygalacturonase-inhibiting protein is described by Toubart et al., (1992 Plant J. 2:367).

(R) A developmental-arrestive protein produced in nature by a plant, such as the barley ribosome-inactivating gene that provides an increased resistance to fungal disease (Longemann et al., 1992 Bio/Technology 10:3305).

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al., U.S. Pat. No. 6,573,099.

2. Genes that Confer Tolerance to a Herbicide (A) Genes encoding resistance or tolerance to a herbicide that inhibits the growing point or meristem, such as an imidazalinone, sulfonanilide, or sulfonylurea herbicides. Exemplary genes in this category code for mutant acetolactate synthase (ALS) (Lee et al., 1988 EMBO J. 7:1241) also known as acetohydroxyacid synthase (AHAS) enzyme (Miki et al., 1990 Theor. Appl. Genet. 80:449).

(B) One or more additional genes encoding resistance or tolerance to glyphosate imparted by mutant EPSP synthase and aroA genes, or through metabolic inactivation by genes such as DGT-28, 2mEPSPS, GAT (glyphosate acetyltransferase) or GOX (glyphosate oxidase) and other phosphono compounds such as glufosinate (pat, bar, and dsm-2 genes), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al., (1989 Bio/Technology 7:61) describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Acc1-S1, Acc1-S2 and Acc1-S3 genes described by Marshall et al., (1992 Theor. Appl. Genet. 83:435).

(C) Genes encoding resistance or tolerance to a herbicide that inhibits photosynthesis, such as a triazine (psbA and gs+ genes) and a benzonitrile (nitrilase gene). Przibilla et al., (1991 Plant Cell 3:169) describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al., (1992 Biochem. J. 285:173).

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2 phenyl)propane-1,3-dione, triketones (EP625505, EP625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. patent application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the a-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the a-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245).

3. Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., 1992 Proc. Nat. Acad. Sci. USA 89:2624).

(B) Decreased phytate content (1) Introduction of a phytase-encoding gene, such as the *Aspergillus niger* phytase gene (Van Hartingsveldt et al., 1993 Gene 127:87), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., 1988 J. Bacteriol. 170:810), *Bacillus subtilis* levansucrase gene (Steinmetz et al., 1985 Mol. Gen. Genel. 200:220), *Bacillus licheniformis* a-amylase (Pen et al., 1992 Bio/Technology 10:292), tomato invertase genes (Elliot et al., 1993 Plant Mol. Biol. 21:515-524), barley amylase gene (Sogaard et al., 1993 J. Biol. Chem. 268:22480), and maize endosperm starch branching enzyme II (Fisher et al., 1993 Plant Physiol. 102:10450).

Transformation

Suitable methods for transformation of plants include any method that DNA can be introduced into a cell, for example and without limitation: electroporation (see, e.g., U.S. Pat. No. 5,384,253); micro-projectile bombardment (see, e.g., U.S. Pat. Nos. 5,015,580; 5,550,318; 5,538,880; 6,160,208; 6,399,861; and 6,403,865); *Agrobacterium*-mediated transformation (see, e.g., U.S. Pat. Nos. 5,635,055; 5,824,877; 5,591,616; 5,981,840; and 6,384,301); and protoplast transformation (see, e.g., U.S. Pat. No. 5,508,184). These methods may be used to stably transform or transiently transform a plant.

A DNA construct may be introduced directly into the genomic DNA of the plant cell using techniques such as agitation with silicon carbide fibers (See, e.g., U.S. Pat. Nos. 5,302,523 and 5,464,765), or the DNA constructs can be introduced directly to plant tissue using biolistic methods, such as DNA particle bombardment (see, e.g., Klein et al., (1987) Nature 327:70-73). Alternatively, the DNA construct can be introduced into the plant cell via nanoparticle transformation (see, e.g., U.S. Patent Publication No. 2009/0104700, incorporated herein by reference in its entirety).

In addition, gene transfer may be achieved using non-*Agrobacterium* bacteria or viruses such as *Rhizobium* sp. NGR234, *Sinorhizoboium meliloti*, *Mesorhizobium loti*, potato virus X, cauliflower mosaic virus and cassava vein mosaic virus and/or tobacco mosaic virus, see, e.g., Chung et al., (2006) *Trends Plant Sci.* 11(1): 1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797; 5,159,135; 5,004,863; and 6,624,344; techniques for transforming *Brassica* plants in particular are described, for example, in U.S. Pat. No. 5,750,871; techniques for transforming soybean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a desired nucleic acid comprising constructs provided in regenerating plants, a variety of assays may be performed. Such assays may include: molecular biological assays, such as Southern and Northern blotting and PCR; biochemical assays, such as detecting the presence of a protein product, e.g., by immunological means (ELISA, western blots, and/or LC-MS MS spectrophotometry), or by enzymatic function; plant part assays, such as leaf or root assays; and/or analysis of the phenotype of the whole regenerated plant.

Transgenic events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al., (2002) Plant J. 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. Primers may be used in conjunction with primers described herein. Oligonucleotide primers may be synthesized according to a desired sequence and are commercially available (e.g., from Integrated DNA Technologies, Inc., Coralville, Iowa). Amplification may be followed by cloning and sequencing, or by direct sequence analysis of amplification products. In an embodiment, oligonucleotide primers specific for the gene target are employed in PCR amplifications.

Method of Expressing a Transgene

In an embodiment, a method of expressing at least one transgene in a plant comprises growing a plant comprising a *Zea mays* chlorophyll a/b binding gene promoter operably linked to at least one transgene. In an embodiment, a method of expressing at least one transgene in a plant comprises growing a plant comprising a *Zea mays* chlorophyll a/b binding gene intron operably linked to at least one transgene. In an embodiment, a method of expressing at least one transgene in a plant comprises growing a plant comprising a *Zea mays* chlorophyll a/b binding gene promoter and intron operably linked to at least one transgene. In an embodiment, a method of expressing at least one transgene in a plant comprising growing a plant comprising a *Zea mays* chlorophyll a/b binding gene 3'-UTR operably linked to at least one transgene. In an embodiment, a method of expressing at least one transgene in a plant comprises growing a plant comprising a *Zea mays* chlorophyll a/b binding gene promoter, intron, and 3'-UTR operably linked to at least one transgene. In an embodiment, a method of expressing at least one transgene in a plant comprising growing a plant comprising a *Zea mays* chlorophyll a/b binding gene 5'-UTR operably linked to at least one transgene. In an embodiment, a method of expressing at least one transgene in a plant comprises growing a plant comprising a *Zea mays* chlorophyll a/b binding gene promoter, intron, and 5'-UTR operably linked to at least one transgene. In an embodiment, a method of expressing at least one transgene in a plant comprising growing a plant comprising a *Zea mays* chlorophyll a/b binding gene promoter operably linked to at least one transgene. In an embodiment, a method of expressing at least one transgene in a plant comprising growing a plant comprising a *Zea mays* chlorophyll a/b binding gene intron operably linked to at least one transgene. In an embodiment, a method of expressing at least one transgene in a plant comprising growing a plant comprising a *Zea mays* chlorophyll a/b binding gene promoter and intron operably linked to at least one transgene. In an embodiment, a method of expressing at least one transgene in a plant comprising growing a plant comprising a *Zea mays* chlorophyll a/b binding gene 3'-UTR operably linked to at least one transgene. In an embodiment, a method of expressing at least one transgene in a plant comprising growing a plant comprising a *Zea mays* chlorophyll a/b binding gene promoter, and a *Zea mays* chlorophyll a/b binding gene 3'-UTR operably linked to at least one transgene. In an embodiment, a method of expressing at least one transgene in a plant comprising growing a plant comprising a *Zea mays* chlorophyll a/b binding gene 5'-UTR operably linked to at least one transgene. In an embodiment, a method of expressing at least one transgene in a plant comprising growing a plant comprising a *Zea mays* chlorophyll a/b binding gene promoter, and a *Zea mays* chlorophyll a/b binding gene 5'-UTR operably linked to at least one transgene.

In an embodiment, a method of expressing at least one transgene in a plant tissue or plant cell comprising culturing a plant tissue or plant cell comprising a *Zea mays* chlorophyll a/b binding gene promoter operably linked to at least one transgene. In an embodiment, a method of expressing at least one transgene in a plant tissue or plant cell comprising culturing a plant tissue or plant cell comprising a *Zea mays* chlorophyll a/b binding gene intron operably linked to at least one transgene. In an embodiment, a method of expressing at least one transgene in a plant tissue or plant cell comprising culturing a plant tissue or plant cell comprising a *Zea mays* chlorophyll a/b binding gene promoter and intron operably linked to at least one transgene. In an embodiment, a method of expressing at least one transgene in a plant tissue or plant cell comprising culturing a plant tissue or plant cell comprising a *Zea mays* chlorophyll a/b binding gene 3'-UTR operably linked to at least one transgene. In an embodiment, a method of expressing at least one transgene in a plant tissue or plant cell comprising culturing a plant tissue or plant cell comprising a *Zea mays* chlorophyll a/b binding gene promoter and a *Zea mays* chlorophyll a/b binding gene 3'-UTR operably linked to at least one transgene. In an embodiment, a method of expressing at least one transgene in a plant tissue or plant cell comprising culturing a plant tissue or plant cell comprising a *Zea mays* chlorophyll a/b binding gene promoter, intron, and 3'-UTR operably linked to at least one transgene. In an embodiment, a method of expressing at least one transgene in a plant tissue or plant cell comprising culturing a plant tissue or plant cell comprising a *Zea mays* chlorophyll a/b binding gene 5'-UTR operably linked to at least one transgene. In an embodiment, a method of expressing at least one transgene in a plant tissue or plant cell comprising culturing a plant tissue or plant cell comprising a *Zea mays* chlorophyll a/b binding gene promoter and a *Zea mays* chlorophyll a/b binding gene 5'-UTR operably linked to at least one transgene. In an embodiment, a method of expressing at least one transgene in a plant tissue or plant cell comprising culturing a plant tissue or plant cell comprising a *Zea mays* chlorophyll a/b binding gene promoter, intron, and 5'-UTR operably linked to at least one transgene.

In an embodiment, a method of expressing at least one transgene in a plant comprises growing a plant comprising a gene expression cassette comprising a *Zea mays* chlorophyll a/b binding gene promoter operably linked to at least one transgene. In an embodiment, a method of expressing at least one transgene in a plant comprises growing a plant comprising a gene expression cassette comprising a *Zea mays* chlorophyll a/b binding gene intron operably linked to at least one transgene. In an embodiment, a method of expressing at least one transgene in a plant comprises growing a plant comprising a gene expression cassette comprising a *Zea mays* chlorophyll a/b binding gene promoter and intron operably linked to at least one transgene. In an embodiment, a method of expressing at least one transgene in a plant comprises growing a plant comprising a gene expression cassette comprising a *Zea mays* chlorophyll a/b binding gene 3'-UTR operably linked to at least one transgene. In an embodiment, a method of expressing at least one transgene in a plant comprises growing a plant comprising a gene expression cassette comprising a *Zea mays* chlorophyll a/b binding gene promoter and a *Zea mays* chlorophyll a/b binding gene 3'-UTR operably linked to at least one transgene. In an embodiment, a method of expressing at least one transgene in a plant comprises growing a plant comprising a gene expression cassette comprising a *Zea mays* chlorophyll a/b binding gene promoter, intron, and 3'-UTR operably linked to at least one transgene. In an embodiment, a method of expressing at least one transgene in a plant comprises growing a plant comprising a gene expression cassette comprising a *Zea mays* chlorophyll a/b binding gene 5'-UTR operably linked to at least one transgene. In an embodiment, a method of expressing at least one transgene in a plant comprises growing a plant comprising a gene expression cassette comprising a *Zea mays* chlorophyll a/b binding gene promoter and a *Zea mays* chlorophyll a/b binding gene 5'-UTR operably linked to at least one transgene. In an embodiment, a method of expressing at least one transgene in a plant comprises growing a plant comprising a gene expression cassette comprising a *Zea mays* chlorophyll a/b binding gene promoter, intron, and 5'-UTR operably linked to at least one transgene.

In an embodiment, a method of expressing at least one transgene in a plant tissue or plant cell comprises culturing a plant tissue or plant cell comprising a gene expression cassette a *Zea mays* chlorophyll a/b binding gene promoter operably linked to at least one transgene. In an embodiment, a method of expressing at least one transgene in a plant tissue or plant cell comprises culturing a plant tissue or plant cell comprising a gene expression cassette a *Zea mays* chlorophyll a/b binding gene intron operably linked to at least one transgene. In an embodiment, a method of expressing at least one transgene in a plant tissue or plant cell comprises culturing a plant tissue or plant cell comprising a gene expression cassette a *Zea mays* chlorophyll a/b binding gene promoter and intron operably linked to at least one transgene. In an embodiment, a method of expressing at least one transgene in a plant tissue or plant cell comprises culturing a plant tissue or plant cell comprising a gene expression cassette a *Zea mays* chlorophyll a/b binding gene 3'-UTR operably linked to at least one transgene. In an embodiment, a method of expressing at least one transgene in a plant tissue or plant cell comprises culturing a plant tissue or plant cell comprising a gene expression cassette a *Zea mays* chlorophyll a/b binding gene promoter and a *Zea mays* chlorophyll a/b binding gene 3'-UTR operably linked to at least one transgene. In an embodiment, a method of expressing at least one transgene in a plant tissue or plant cell comprises culturing a plant tissue or plant cell comprising a gene expression cassette comprising a *Zea mays* chlorophyll a/b binding gene promoter, intron, and 3'-UTR operably linked to at least one transgene. In an embodiment, a method of expressing at least one transgene in a plant tissue or plant cell comprises culturing a plant tissue or plant cell comprising a gene expression cassette a *Zea mays* chlorophyll a/b binding gene 5'-UTR operably linked to at least one transgene. In an embodiment, a method of expressing at least one transgene in a plant tissue or plant cell comprises culturing a plant tissue or plant cell comprising a gene expression cassette a *Zea mays* chlorophyll a/b binding gene promoter and a *Zea mays* chlorophyll a/b binding gene 5'-UTR operably linked to at least one transgene. In an embodiment, a method of expressing at least one transgene in a plant tissue or plant cell comprises culturing a plant tissue or plant cell comprising a gene expression cassette comprising a *Zea mays* chlorophyll a/b binding gene promoter, intron, and 5'-UTR operably linked to at least one transgene.

In an embodiment, a plant, plant tissue, or plant cell comprises a *Zea mays* chlorophyll a/b binding gene promoter (also including an upstream-promoter). In an embodiment, a *Zea mays* chlorophyll a/b binding gene promoter can be SEQ ID NO:1, SEQ ID NO:2, SEQ ID NO:3, or SEQ ID NO:4. In an embodiment, a plant, plant tissue, or plant cell comprises a gene expression cassette comprising a *Zea mays* chlorophyll a/b binding gene promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, SEQ ID NO:2, SEQ ID NO:3, or SEQ ID NO:4. In an embodiment, a plant, plant tissue, or plant cell comprises a gene expression cassette comprising a *Zea mays* chlorophyll a/b binding gene promoter that is operably linked to a transgene. In an illustrative embodiment, a plant, plant tissue, or plant cell comprises a gene expression cassette comprising a *Zea mays* chlorophyll a/b binding gene promoter that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising an intron. In an embodiment, a plant, plant tissue, or plant cell comprises a gene expression cassette comprising a *Zea mays* chlorophyll a/b binding gene intron. In an embodiment, the *Zea mays* chlorophyll a/b binding gene intron is a polynucleotide of SEQ ID NO:5 or SEQ ID NO:6. In an embodiment, a plant, plant tissue, or plant cell comprises a gene expression cassette comprising an intron, wherein the intron is at least 80%, 85%, 90%, 91%, 92%, 93%, 94%, 95%, 96%, 97%, 98%, 99%, 99.5%, 99.8%, or 100% identical to SEQ ID NO:5 or SEQ ID NO:6. In an embodiment, a gene expression cassette comprises a *Zea mays* chlorophyll a/b binding gene intron that is operably linked to a promoter, wherein the promoter is a *Zea mays* promoter, or a promoter that originates from a plant (e.g., *Zea mays* chlorophyll a/b binding gene promoter or *Zea mays* ubiquitin 1 promoter), a virus (e.g., Cassava vein mosaic virus promoter), or a bacteria (e.g., *Agrobacterium tumefaciens* delta mas). In an embodiment, a plant, plant tissue, or plant cell comprises a gene expression cassette comprising a *Zea mays* chlorophyll a/b binding gene intron that is operably linked to a transgene. In an illustrative embodiment, a plant, plant tissue, or plant cell comprising a gene expression cassette comprising a *Zea mays* chlorophyll a/b binding gene intron that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Zea mays* chlorophyll a/b binding gene 3'-UTR. In an embodiment, a plant, plant tissue, or plant cell comprises a gene expression cassette comprising a *Zea mays* chlorophyll a/b binding gene 3'-UTR. In an embodiment, the *Zea mays* chlorophyll a/b binding gene 3'-UTR is a polynucleotide of SEQ ID NO:7 or SEQ ID NO:8. In an embodiment, a plant, plant tissue, or plant cell comprises a gene expression cassette comprising a *Zea mays* chlorophyll a/b binding gene 3'-UTR, wherein the *Zea mays* chlorophyll a/b binding gene 3'-UTR is at least 80%, 85%, 90%, 91%, 92%, 93%, 94%, 95%, 96%, 97%, 98%, 99%, 99.5%, 99.8%, or 100% identical to SEQ ID NO:7 or SEQ ID NO:8. In an embodiment, a gene expression cassette comprises a *Zea mays* chlorophyll a/b binding gene 3'-UTR that is operably linked to a promoter, wherein the promoter is a *Zea mays* chlorophyll a/b binding gene promoter, or a promoter that originates from a plant (e.g., *Zea mays* ubiquitin 1 promoter), a virus (e.g., Cassava vein mosaic virus promoter), or a bacteria (e.g., *Agrobacterium tumefaciens* delta mas). In an embodiment, a plant, plant tissue, or plant cell comprises a gene expression cassette comprising a *Zea mays* chlorophyll a/b binding gene 3'-UTR that is operably linked to a transgene. In an illustrative embodiment, a plant, plant tissue, or plant cell comprising a gene expression cassette comprising a *Zea mays* chlorophyll a/b binding gene 3'-UTR that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Zea mays* chlorophyll a/b binding gene 5'-UTR. In an embodiment, a plant, plant tissue, or plant cell comprises a gene expression cassette comprising a *Zea mays* chlorophyll a/b binding gene 5'-UTR. In an embodiment, the *Zea mays* chlorophyll a/b binding gene 5'-UTR is a polynucleotide of SEQ ID NO:19. In an embodiment, a plant, plant tissue, or plant cell comprises a gene expression cassette comprising a *Zea mays* chlorophyll a/b binding gene 5'-UTR, wherein the *Zea mays* chlorophyll a/b binding gene 5'-UTR is at least 80%, 85%, 90%, 91%, 92%, 93%, 94%, 95%, 96%, 97%, 98%, 99%, 99.5%, 99.8%, or 100% identical to SEQ ID NO:19. In an embodiment, a gene expression cassette comprises a *Zea mays* chlorophyll a/b binding gene 5'-UTR that is operably linked to a promoter, wherein the promoter is a *Zea mays* chlorophyll a/b binding gene promoter, or a promoter that originates from a plant (e.g., *Zea mays* ubiquitin 1 promoter), a virus (e.g., Cassava vein mosaic virus promoter), or a bacteria (e.g., *Agrobacterium tumefaciens* delta mas). In an embodiment, a plant, plant tissue, or plant cell comprises a gene expression cassette comprising a *Zea mays* chlorophyll a/b binding gene 5'-UTR that is operably linked to a transgene. In an illustrative embodiment, a plant, plant tissue, or plant cell comprising a gene expression cassette comprising a *Zea mays* chlorophyll a/b binding gene 5'-UTR that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Zea mays* chlorophyll a/b binding gene promoter and *Zea mays* chlorophyll a/b binding gene intron that are operably linked to a transgene. The promoter, intron, 3'-UTR, and 5'-UTR can be operably linked to different transgenes within a gene expression cassette when a gene expression cassette includes two or more transgenes. In an illustrative embodiment, a gene expression cassette comprises a *Zea mays* chlorophyll a/b binding gene promoter that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* chlorophyll a/b binding gene intron that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Zea mays* chlorophyll a/b binding gene promoter, *Zea mays* chlorophyll a/b binding gene intron, and a *Zea mays* chlorophyll a/b binding gene 3'-UTR that are operably linked to a transgene. The promoter, intron, and 3'-UTR can be operably linked to different transgenes within a gene expression cassette when a gene expression cassette includes two or more transgenes. In an illustrative embodiment, a gene expression cassette comprises a *Zea mays* chlorophyll a/b binding gene promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* chlorophyll a/b binding gene intron that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* chlorophyll a/b binding gene 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Zea mays* chlorophyll a/b binding gene promoter, *Zea mays* chlorophyll a/b binding gene intron, a *Zea mays* chlorophyll a/b binding gene 3'-UTR, and a *Zea mays* chlorophyll a/b binding gene 5'-UTR that are operably linked to a transgene. The promoter, intron, 3'-UTR, and 5'-UTR can be operably linked to different transgenes within a gene expression cassette when a gene expression cassette includes two or more transgenes. In an illustrative embodiment, a gene expression cassette comprises a *Zea mays* chlorophyll a/b binding gene promoter that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* chlorophyll a/b binding gene intron that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* chlorophyll a/b binding gene 5'-UTR that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

In an embodiment, transgene expression using methods described herein is expressed within a plant's leaf and stem tissues. In an embodiment, transgene expression includes more than one transgene expressed in the plant's leaf and stem tissues. In an embodiment, a method of growing a transgenic plant as described herein includes leaf and stem-preferred transgene expression. In an embodiment, a method of expressing a transgene in a plant tissue or plant cell includes leaf and stem-preferred tissues and leaf and stem-preferred cells. In an embodiment, the leaf and stem-preferred expression includes maize leaf and stem-preferred expression.

In a further embodiment, transgene expression using methods described herein is expressed within above ground plant tissues (e.g., above ground plant tissues include leaf, husk, stem, and silk). In an embodiment, transgene expression includes more than one transgene expressed in above ground plant tissues. In an embodiment, a method of growing a transgenic plant as described herein includes above ground plant tissues transgene expression. In an embodiment, a method of expressing a transgene in a plant tissue or plant cell above ground plant tissues and above ground plant cells. In an embodiment, the above ground plant tissue expression includes maize above ground plant tissue expression.

In an embodiment, a plant, plant tissue, or plant cell comprises a vector comprising a *Zea mays* chlorophyll a/b binding gene promoter, intron, 3'-UTR, or 5'-UTR regulatory element as disclosed herein. In an embodiment, a plant, plant tissue, or plant cell comprises a vector comprising a *Zea mays* chlorophyll a/b binding gene promoter, intron, 3'-UTR, or 5'-UTR regulatory element as disclosed herein operably linked to a transgene. In an embodiment, a plant, plant tissue, or plant cell comprises a vector comprising a gene expression cassette as disclosed herein. In an embodiment, a vector can be a plasmid, a cosmid, a bacterial artificial chromosome (BAC), a bacteriophage, or a virus fragment.

In an embodiment, a plant, plant tissue, or plant cell according to the methods disclosed herein can be monocotyledonous. The monocotyledon plant, plant tissue, or plant cell can be, but not limited to, corn, rice, wheat, sugarcane, barley, rye, sorghum, orchids, bamboo, banana, cattails, lilies, oat, onion, millet, and triticale.

In an embodiment, a plant, plant tissue, or plant cell according to the methods disclosed herein can be dicotyledonous. The dicotyledonous plant, plant tissue, or plant cell can be, but is not limited to rapeseed, canola, Indian mustard, Ethiopian mustard, soybean, sunflower, and cotton.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Goto-Fumiyuki et al., *Nature Biotech* 17:282-286 (1999); Miki et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue, or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the yfp, gfp, β-glucuronidase, luciferase, B or Cl genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) next generation sequencing (NGS) analysis; 5) protein gel electrophoresis, western blot techniques, immunoprecipitation, or enzyme-linked immunosorbent assay (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, Northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 (aryloxyalkanoate dioxygenase; see WO 2005/107437) and PAT (phosphinothricin-N-acetyltransferase) proteins using an ELISA assay is described in U.S. Patent Publication No. 20090093366 which is herein incorporated by reference in its entirety. The transgene may be selectively expressed in some cell types or tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed comprises the transgene or gene expression cassette. The present disclosure further encompasses the progeny, clones, cell lines or cells of the transgenic plants described above wherein said progeny, clone, cell line or cell comprise the transgene or gene construct.

While the invention has been described with reference to specific methods and embodiments, it will be appreciated that various modifications and changes may be made without departing from the invention.

EXAMPLES

Example 1

Identification of High Expressing Regulatory Elements

Novel *Zea mays* chlorophyll a/b binding gene regulatory elements were identified via a transcriptional profiling approach by using Next Generation Sequencing (NGS). These regulatory elements were then identified, isolated, and cloned to characterize the expression profile of the regulatory elements for use in of transgenic plants. Transgenic maize lines stably transformed with a cry34Ab1 gene isolated from *Bacillus thuringiensis* and an aad-1 selectable marker gene were produced and the transgene expression levels and tissue specificity was assessed. As such novel *Zea mays* chlorophyll a/b binding gene regulatory elements were identified and characterized. Disclosed for the first time are promoter, intron, 5' UTR, and 3'-UTR regulatory elements for use in gene expression constructs.

Transcriptional Profiling Approach:

Maize tissues were obtained from plants grown to different stages of plant growth and development for transcriptional profiling in order to identify and select regulatory elements of native maize genes with desired expression profiles for use in gene expression cassettes. For example, tissue samples from four stages of leaf (V4 (duplicate), V12 and R3) and four stages of root (V4 and V12 nodal and fibrous tissues) development, pollen, silk, cob, immature kernel (20 days after pollination), husk and stem (V4 and R1) were collected. Total mRNA was isolated from all of the above described tissues and high quality mRNA in desired quantities was obtained.

Next, cDNA libraries were prepared from each of the mRNA samples and high-throughput sequencing was completed using an ILLUMINA HISEQ® 2000 (Illumina Inc., San Diego, Calif.). In addition, the ILLUMINA TRUSEQ® RNA sample preparation kit was used according to the manufacturer's recommended protocol for RNAseq sample preparation. In brief, 5 µg of total RNA was purified using poly-T oligo-attached magnetic beads followed by fragmentation into smaller pieces (about 200 bp average length) using divalent cations under high temperature. Next, SUPERSCRIPT® II reverse transcriptase and random primers were then used to copy the fragmented mRNA into first strand cDNA. The cDNA was further converted into double stranded cDNA (ds cDNA) using DNA polymerase I and RNase H. The double stranded cDNA fragments then went through end repair, A-tailing, and then ligation to indexed Illumina paired-end (PE) adapters. Finally, library products were cleaned up and enriched with 15 cycles of PCR and purified. The enriched libraries were normalized to a concentration of 2 nM, denatured with sodium hydroxide, and diluted to 12 pM in hybridization buffer for loading onto a single lane of a HISEQ® flow cell. Cluster generation, primer hybridization and sequencing reactions were carried out according to an Illumina manufacturer recommended sequencing protocol.

The sequencing reads were then filtered to remove low quality reads. About 99.9% of the sequencing reads were retained after filtering. The sequencing reads were aligned to the annotated *Zea mays* c.v. B73 genome available in the maizeGDB. Sequencing reads that mapped onto the maize genome at more than one locus were discarded to avoid confusion in identification of the high expressing genes and their further characterization. This step led to alignment of >70% sequencing reads from each of the samples to the maize genome. The quantitative gene expression unit of fragments per kilobase of exon per million fragments mapped (or FPKM values) were used to rank genes for stable transformation testing that matched a desirable expression pattern for use in gene expression constructs. Approximately 15-20 high expressing genes, which represented ~0.1% of the most highly expressed genes in maize were prioritized for testing in stable transgenic lines (FIG. 1).

Example 2

Gene Regulatory Element Identification

The promoter, intron, 5'-UTR, and 3'-UTR sequences were extracted from the *Zea mays* chlorophyll a/b binding gene sequence that was identified from the bioinformatics and transcriptional profiling approaches previously described. The isolated and purified sequence of the *Zea mays* chlorophyll a/b binding gene, from the *Zea* may c.v. B73 genome is provided as SEQ ID NO:9. The full length 2,006 bp promoter sequence (SEQ ID NO:1) comprise base pairs 1-2006 of SEQ ID NO:9. The 1,887 bp upstream promoter sequence (SEQ ID NO:2) comprises base pairs 1-1,887 of SEQ ID NO:9. The 59 bp intron sequence (SEQ ID NO:5) comprises base pairs 1,888-1,946 of SEQ ID NO:9. The 60 bp 5'-UTR sequence (SEQ ID NO:19) comprises base pairs 1,947-2,006 of SEQ ID NO:9. The ATG and TGA translational start and stop codons flanking the coding sequence comprise base pairs 2,007-2,009 and 2,802-2,804, respectively, of SEQ ID NO:9. The 1,000 bp 3'-UTR sequence (SEQ ID NO:7) comprises base pairs 2,805-3,804 of SEQ ID NO:9. A second 43 bp intron (SEQ ID NO:6) is identified within the 3'UTR and comprises base pairs 2,809-2,851 of SEQ ID NO:9.

The DNA elements were either amplified or synthesized and cloned into entry vectors. The full length promoter and full length 3'-UTR sizes were 2,006 bp and 1,000 bp, respectively.

Example 3

Modifications of the *Zea Mays* Chlorophyll A/B Binding Gene Promoter and 3'-UTR Sequences The *Zea mays* chlorophyll a/b binding gene promoter sequence was modified. Repeated sequences were identified and removed thereby resulting in a modified *Zea mays* chlorophyll a/b binding gene promoter sequence of:

```
                                            (SEQ ID NO: 3)
GCACAAAATACATAAAACTAGATTAGAAAAGGAAGAGAATACGCCAAATT

GCAGCTTAATCAATTAGACGATTTAGTCCTGTTTTTACGAAACAATTGTT

TAAGATAACATGGCCTTATACTTGGAGTTTGGCATGTCTTATGCTATGTT

GCAAACAGGCCCGGTCTTGACATTTCGGGGGCCCTAAGAGAAAATTTATA

TAGAGGTCCTATACGAAAATTTGAGTCTGTTATTTTTTCAACTTTTAAAT

AATATATGAAAAATAAAAAATTGATGATTTACATAATTTTATTCAAAATG

ATATGACTGGAAATATTGTTACAGTATTTTATGAGTCGTAAAATTATATA

AATTATGTAATATACATTTGTTTTGACTTTTGAGAGAGTATTTTTACTTT

TAATTTGTCAAACTAGCCTAAACCTTAAAATACACAGTAAACCAAATCTA

AATACATTAGATCAAATTTTCTGAAAATAAAGTTCAGCAAACTAAACTAG

GATTAATCAATGTAGGTTATTAGGGTCGACCCTTCGGTAGGCTAGAATTA

AGCAACGCGATAGGCACAGGTGTACAACACCTTTCGTCCTTCCCACGTCA

ATAAAGTATTTGTCATCAAGCAGACGGTTGCGCGACCTCAAAGAGATGAT
```

```
-continued
TGCTAGAAAATAAAGAGACGCAACAAAAGAATGAAAATATAGATTTATCT

ATAACTTATATGCATTTGATATAAGATAGATAAATGGGAGCCCTACGAAC

CTTGAGGCTCTGAGCAGTCGCATATCCTGCACACCCTTGGCGCCGGCCCT

GGTTGCAAATATGCAATTGTGTCCTTATCCGCGACTGGTCACGAGGCTAG

GATTGATCGAAAGCTGCCGATGAGAAATGGCAAGGGCGGCATGCTGTGGC

CTTTTTTTTACGGTCTGTCAGGACAACTGAAAAGTTACAAATTTATAGTG

GTTGTAAACAGCAACACGTTAAAAAGTCGATTATCAGTTTCACAGAAAGA

GGTCGTTAAAACCGCCAGCAAGCTTGTTTCACTATCAGTCTGTCGCTAAG

ACAATCTCTTTCACCAAAAATACAATTTGCTTTCTTGCCGTTGCTTCAAG

TGAAAATCTGAGCTAAAAAAGAGAGAGGCTGTCTGAAGAAAAATCCATAA

CCAACGCAAAATCCCGGGCGCCCAATCAGCCTTCTCCGCGGAGATTCCTA

GCCTCAGCCAGAGCTACCTCATCTGCGTGAGGCTCCGGTGGCGCCAAGTG

TTCCGGCATCCCGGACGCACCAATGGCATCCGAGCAACAGATCTTTTCTG

CAACAACGCTTCGCGTCGCGGCGGTGTTTCCCTCCATCTGCTCTGCTCTT

TAAATACCTCCGTCGTCTCCTCGTCTCCACAGCATCTCAAGTCTTCACAC

TCCTCGCCATCACATAAAACCAGTGCAAGCAGAAGCAGCGCA
```

FIG. 2 provides an alignment of the full length *Zea mays* chlorophyll a/b binding gene promoter (SEQ ID NO:1) as compared to the modified *Zea mays* chlorophyll a/b binding gene promoter (SEQ ID NO:3), this alignment shows the repeated polynucleotide sequences that were removed to produce the modified *Zea mays* chlorophyll a/b binding gene promoter sequence.

Next, the *Zea mays* chlorophyll a/b binding gene 3'-UTR sequence (SEQ ID NO:7) was modified. The 3'-UTR was truncated to a 400 bp polynucleotide sequence, thereby resulting in a modified *Zea mays* chlorophyll a/b binding gene 3'-UTR sequence (SEQ ID NO:8) of:

```
                                            (SEQ ID NO: 8)
GGGGGTGGAGGCGCCACCGCCCACCGGCCACCGCTGCGGATATCTAGGTG

TTCGGATGCACGTGAGCGCGCACTGGTTCCAGTTTGTACCATGATGTAAA

TTACTTACCGTACCAGGGTTCAATCGGCAAGGAAGAATTGTTGTGTTCAC

TGTCTTGGGCAGTCTCTTGGTCCAATATGAATCAACTTACACAGCATCTC

CAAAAACTTCTAAAATTACTAGCTGAATGCCCGTGCGTTGCAACGGGAAT

ATATAATACCAGTATACTACGATAACTTATATACAAAATGTATGTTATAT

CGTTATGAGAAAATGTTTCATAACCAATTTATGATTCTGGTCATACATAA

ATTTTGTTATTTATAGTCTATCTGTTTCACCACTACATTGCAACCATCAG
```

The DNA elements were either amplified or synthesized and cloned into entry vectors. The modified promoter and modified 3'-UTR lengths were 1,442 bp and 400 bp, respectively.

Example 4

*Zea Mays* Chlorophyll A/B Binding Gene Promoter Construct

The full length *Zea mays* chlorophyll a/b binding gene upstream promoter of SEQ ID NO:2 linked with the *Zea*

*mays* chlorophyll a/b binding gene intron of SEQ ID NO:5 and a 5' UTR sequence (SEQ ID NO:19) resulted in the full length *Zea mays* chlorophyll a/b binding gene promoter of SEQ ID NO:1. Expression of cry34Ab1 (reporter gene from *B. thurengiensis*) was driven by the full length *Zea mays* chlorophyll a/b binding gene promoter (SEQ ID NO:1), and was terminated by the *Solanum tuberosum* PinII 3'-UTR (StPinII 3'-UTR v2; An et al., (1989) *Plant Cell* 1; 115-22). Each of the gene elements were amplified with primers containing a minimum 15 bp overlapping homology to their flanking DNA element. All fragments were gel purified. Next, the three fragments along with an entry vector backbone, pENTR11, were assembled in a directional order through a GENEART® Seamless cloning reaction (Invitrogen, Carlsbad, Calif.). A GATEWAY® LR CLONASE® (Invitrogen) reaction was then performed with the resulting entry plasmid and a destination vector leading to a final expression vector, pDAB114438. The destination vector contained a selectable marker cassette comprised of an aad-1 gene driven by the full length *Zea mays* ubiquitin-1 promoter (Christensen et al., (1992) *Plant Molecular Biology* 18; 675-689) and terminated by a maize lipase 3'-UTR (U.S. Pat. No. 7,179,902). The resulting construct, pDAB114438 is a heterologous expression construct that contains an aad-1 gene expression cassette and a cry34Ab1 gene expression construct (FIG. 3).

In a second construct, the expression of cry34Ab1 (reporter gene from *B. thurengiensis*) was driven by the full length *Zea mays* chlorophyll a/b binding gene promoter (SEQ ID NO:1), and was terminated by the modified *Zea mays* chlorophyll a/b binding gene 3'-UTR (SEQ ID NO:8). Each of the gene elements were amplified with primers containing a minimum 15 bp overlapping homology to their flanking DNA element. All fragments were gel purified. Next, the three fragments along with an entry vector backbone, pENTR11, were assembled in a directional order through a GENEART® Seamless cloning reaction (Invitrogen, Carlsbad, Calif.). A GATEWAY® LR CLONASE® (Invitrogen) reaction was then performed with the resulting entry plasmid and a destination vector leading to a final expression vector, pDAB120166. The destination vector contained a selectable marker cassette comprised of an aad-1 gene driven by the *Zea mays* ubiquitin-1 promoter (Christensen et al., (1992) *Plant Molecular Biology* 18; 675-689) and terminated by a maize lipase 3'-UTR (U.S. Pat. No. 7,179,902). The resulting construct, pDAB120166 is a heterologous expression construct that contains an aad-1 gene expression cassette and a cry34Ab1 gene expression construct (FIG. 7).

In a third construct, the expression of cry34Ab1 (reporter gene from *B. thurengiensis*) was driven by the modified *Zea mays* chlorophyll a/b binding gene promoter. The modified *Zea mays* chlorophyll a/b binding gene upstream promoter of SEQ ID NO:4 linked with the *Zea mays* chlorophyll a/b binding gene intron of SEQ ID NO:5 and a 5' UTR sequence (SEQ ID NO:19) resulted in the modified *Zea mays* chlorophyll a/b binding gene promoter of SEQ ID NO:3. Expression of the cry34Ab1 (reporter gene from *B. thurengiensis*) was driven by the modified *Zea mays* chlorophyll a/b binding gene promoter (SEQ ID NO:3), and was terminated by the *Solanum tuberosum* PinII 3'-UTR (StPinII 3'-UTR v2; An et al., (1989) *Plant Cell* 1; 115-22). Each of the gene elements were amplified with primers containing a minimum 15 bp overlapping homology to their flanking DNA element. All fragments were gel purified. Next, the three fragments along with an entry vector backbone, pENTR11, were assembled in a directional order through a GENEART® Seamless cloning reaction (Invitrogen, Carlsbad, Calif.). A GATEWAY® LR CLONASE® (Invitrogen) reaction was then performed with the resulting entry plasmid and a destination vector leading to a final expression vector, pDAB120165. The destination vector contained a selectable marker cassette comprised of an aad-1 gene driven by the modified *Zea mays* ubiquitin-1 promoter (Christensen et al., (1992) *Plant Molecular Biology* 18; 675-689) and terminated by a maize lipase 3'-UTR (U.S. Pat. No. 7,179,902). The resulting construct, pDAB120165 is a heterologous expression construct that contains an aad-1 gene expression cassette and a cry34Ab1 gene expression construct (FIG. 6).

A negative control construct, pDAB101556, was assembled containing a yellow fluorescence protein (YFP; Shagin et al., (2004) *Mol Biol Evol* 21; 841-50) reporter gene instead of the cry34Ab1 gene (FIG. 4) and the same aad-1 expression cassette as present in pDAB114438. A positive control construct, pDAB108746, was built comprised of the *Zea mays* ubiquitin-1 promoter and *Solanum tuberosum* protease inhibitor gene II 3' UTR (StPinII 3'-UTR v2; An et al., (1989) *Plant Cell* 1; 115-22) controlling the expression of the cry34Ab1 gene (FIG. 5). The aad-1 cassette was the same as present in pDAB114438.

Example 5

Plant Transformation and Molecular Confirmation Transformation of *Agrobacterium tumefaciens*

The binary expression vectors were transformed into *Agrobacterium tumefaciens* strain DAt13192 (RecA deficient ternary strain) (Int'l. Pat. Pub. No. WO2012016222). Bacterial colonies were selected, and binary plasmid DNA was isolated and confirmed via restriction enzyme digestion.

*Agrobacterium* Culture Initiation:

*Agrobacterium* cultures were streaked from glycerol stocks onto AB minimal medium (Gelvin, S., 2006, *Agrobacterium* Virulence Gene Induction, in Wang, K., ed., *Agrobacterium Protocols Second Edition Vol.* 1, Humana Press, p. 79; made without sucrose and with 5 g/L glucose and 15 g/L BACTO™ Agar) and incubated at 20° C. in the dark for 3 days. *Agrobacterium* cultures were then streaked onto a plate of YEP medium (Gelvin, S., 2006, *Agrobacterium* Virulence Gene Induction, in Wang, K., ed., *Agrobacterium Protocols Second Edition Vol.* 1, Humana Press, p. 79) and incubated at 20° C. in the dark for 1 day.

On the day of an experiment, a mixture of Inoculation medium (2.2 g/L MS salts, 68.4 g/L sucrose, 36 g/L glucose, 115 mg/L L-proline, 2 mg/L glycine, 100 mg/L myo-Inositol, 0.05 mg/L nicotinic acid, 0.5 mg/L pyridoxine HCl, 0.5 mg/L thiamine HCl) and acetosyringone was prepared in a volume appropriate to the size of the experiment. A 1 M stock solution of acetosyringone in 100% dimethyl sulfoxide was added to the Inoculation medium to make a final acetosyringone concentration of 200 μM.

For each construct, 1-2 loops of *Agrobacterium* from the YEP plate were suspended in 15 ml of the inoculation medium/acetosyringone mixture inside a sterile, disposable, 50 ml centrifuge tube and the optical density of the solution at 600 nm ($O.D._{600}$) was measured in a spectrophotometer. The suspension was then diluted down to 0.25-0.35 $O.D._{600}$ using additional Inoculation medium/acetosyringone mixture. The tube of *Agrobacterium* suspension was then placed horizontally on a platform shaker set at about 75 rpm at room temperature for between 1 and 4 hours before use.

Maize Transformation:

Experimental constructs were transformed into maize via *Agrobacterium*-mediated transformation of immature embryos isolated from the inbred line, *Zea mays* c.v. B104. The method used is similar to those published by Ishida et al., (1996) Nature Biotechnol 14:745-750 and Frame et al., (2006) Plant Cell Rep 25: 1024-1034, but with several modifications and improvements to make the method amenable to high-throughput transformation. An example of a method used to produce a number of transgenic events in maize is given in U.S. Pat. App. Pub. No. US 2013/0157369 A1, beginning with the embryo infection and co-cultivation steps.

Molecular Confirmation:

Putative transgenic maize plants were sampled at the V2-3 leaf stage for transgene presence using cry34Ab1 and aad-1 quantitative PCR assays. Total DNA was extracted from 4 leaf punches, using MAGATTRACT® DNA extraction kit (Qiagen) as per manufacturer's instructions.

To detect the genes of interest, gene-specific DNA fragments were amplified with TAQMAN® primer/probe sets containing a FAM-labeled fluorescent probe for the cry34Ab1 gene and a HEX-labeled fluorescent probe for the endogenous invertase reference gene control. The following primers were used for the cry34Ab1 and invertase endogenous reference gene amplifications. The primer sequences were as follows;

```
Cry34Ab1 Primers/probes:
Forward Primer: TQ.8v6.1.F:
                                         (SEQ ID NO: 10)
GCCATACCCTCCAGTTG Reverse Primer: TQ.8v6.1.R:
                                         (SEQ ID NO: 11)
GCCGTTGATGGAGTAGTAGATGG Probe: TQ.8v6.1.MGB.P:
                                         (SEQ ID NO: 12)
5'-/56-FAM/ CCGAATCCAACGGCTTCA / MGB Invertase Primers:
Forward Primer: InvertaseF:
                                         (SEQ ID NO: 13)
TGGCGGACGACGACTTGT Reverse Primer: InvertaseR:
                                         (SEQ ID NO: 14)
AAAGTTTGGAGGCTGCCGT InvertaseProbe:
                                         (SEQ ID NO: 15)
5'-/5HEX/CGAGCAGACCGCCGTGTACTT /3BHQ_1/-3'
```

Next, the PCR reactions were carried out in a final volume of 10 µl reaction containing 5 µl of Roche LIGHTCYCLER® 480 Probes Master Mix (Roche Applied Sciences, Indianapolis, Ind.); 0.4 µl each of TQ.8v6.1.F, TQ.8v6.1.R, Invertase F, and InvertaseR primers from 10 µM stocks to a final concentration of 400 nM; 0.4 µl each of TQ.8v6.1.MGB.P and Invertase Probes from 5 µM stocks to a final concentration of 200 nM, 0.1 µl of 10% polyvinylpyrrolidone (PVP) to final concentration of 0.1%; 2 µl of 10 ng/µl genomic DNA and 0.5 µl water. The DNA was amplified in a Roche LIGHTCYCLER® 480 System under the following conditions: 1 cycle of 95° C. for 10 min; 40 cycles of the following 3-steps: 95° C. for 10 seconds; 58° C. for 35 seconds and 72° C. for 1 second, and a final cycle of 4° C. for 10 seconds. Cry34Ab1 copy number was determined by comparison of Target (gene of interest)/Reference (Invertase gene) values for unknown samples (output by the LIGHTCYCLER® 480) to Target/Reference values of cry34Ab1 copy number controls.

The detection of the aad-1 gene was carried out as described above for the cry34Ab1 gene using the invertase endogenous reference gene. The aad-1 primer sequences were as follows;

```
AAD1 Forward Primer:
                                         (SEQ ID NO: 16)
TGTTCGGTTCCCTCTACCAA AAD1 Reverse Primer:
                                         (SEQ ID NO: 17)
CAACATCCATCACCTTGACTGA AAD1 Probe:
                                         (SEQ ID NO: 18)
5'-FAM/CACAGAACCGTCGCTTCAGCAACA-MGB/BHQ-3'
```

Finally, the $T_0$ plants containing the gene of interest were sampled at V4-5 for cry34Ab1 and AAD-1 leaf ELISA assays. Four leaf punches were sampled. Another set of plants were sampled at V4-5 for the entire root mass for both the protein ELISA assays. Leaf and root Cry34Ab1 (Agdia, Inc., Elkart, Ind.) and AAD-1 (Acadia BioScience) ELISA assays were performed as per the manufacturer's instructions. The Cry34Ab1 leaf ELISA assays were expressed as $ng/cm^2$ or as parts per million (ppm, or ng protein per mg total plant protein) while the root ELISA results were expressed as ppm. Total root protein assays were carried out with the Bradford detection method as per the manufacturer's instructions.

$T_0$ plants were crossed to Zea mays c.v. B104 non-transgenic transformation lines to obtain $T_1$ seed. Three transgenic lines or events of each of the test regulatory element constructs were advanced for $T_1$ protein and RNA gene expression studies and then to $T_2$ seed production. Accordingly, 30-40 $T_1$ seed of each of the events were sown; seedlings were sprayed with ASSUREII® at the V2-V3 stage of development to kill non-transgenic segregants. The transgenic plants were sampled at multiple stages of plant development for cry34Ab1 and AAD-1 ELISA as follows: leaf (V4, V12 and R3); root (V4 and R1); stem (R1); pollen (R1); silk (R1); husk (R3); kernel (R3); and cob (R3). All tissues were isolated and placed in tubes embedded in dry ice; which were then transferred to −80° C. Frozen tissues were lyophilized prior to protein extraction for ELISA.

Putative transgenic $T_1$ plants containing cry34Ab1, yfp and aad-1 transgenes were sampled at V4-5 for the leaf ELISA assays. Four leaf punches were sampled. The leaf punches were placed into a tube and a single ⅛" stainless steel bead (Hoover Precision Products, Cumming, Ga., USA) was added to each 1.2 ml tube containing 300 µl extraction buffer (1×PBST supplemented with 0.05% Tween 20 and 0.5% BSA). The samples were processed in a GENOGRINDER™ (SPEX SamplePrep, Metuchen, N.J.) at 1,500 rpm for 4 minutes. The samples were centrifuged at 4,000 rpm for 2 minutes in a Sorvall Legend XFR™ centrifuge. Next, an additional 300 µl of extraction buffer was added and the samples were processed once more in a GENOGRINDER™ at 1,500 rpm for 2 minutes. The samples were centrifuged once more at 4,000 rpm for 7 minutes. Finally, the supernatant was collected and ELISA assays were completed at different dilutions along with the protein standards using the commercially available Cry34Ab1 (Agdia, Inc.) and AAD-1 (Acadia BioScience, LLC) ELISA assay kits, per the manufacturer's instructions. Protein extraction for various tissue type ELISAs was carried out by grinding the lyophilized tissue in a paint shaker for 30 seconds. For tissues needing further grinding, the grinding step was repeated for another 30 seconds. Garnet powder was added to cover the curved portion at the bottom of the tube. The coarsely ground tissue was transferred to 2 ml tubes and filled up to the 0.5 ml mark. One ceramic ball was added to each tube, as was 0.6 ml of the partial extraction buffer (200 µl of protease inhibitor cocktail, 200 µl of 500 mM EDTA, 15.5 mg DTT powder and PBST to 20 ml). All of the tubes were kept on ice for 10 minutes. The cold tubes were transferred to the 2 ml holder of the GENOGRINDER™ The samples were ground twice for 30 seconds with a 5 minute cooling on ice in between. Next, 40 µl of 10% TWEEN®-20 and 300 µl extraction buffer were added to the samples. The samples were ground for another 30 seconds with 5 minutes of cooling in between. Finally, each sample was centrifuged at 13,000 rpm for 7 minutes, and the supernatant was carefully transferred to a new tube to collect the extract. The extract was re-suspended in the extraction buffer and was diluted as needed for ELISA assays leaf tissues.

Example 6

$T_0$ Transgenic Plant Expression

The Cry34Ab1 ELISA results indicated that the full length Zea mays chlorophyll a/b binding gene promoter regulatory element (SEQ ID NO:1 and SEQ ID NO:2) drove leaf preferred expression of Cry34Ab1 in $T_0$ events that were transformed with construct, pDAB114438. Negligible expression of Cry34Ab1 by the full length Zea mays chlorophyll a/b binding gene promoter regulatory element was observed in the root tissues of these events (Tables 1 and 2). The events produced from the positive control construct pDAB108746 expressed Cry34Ab1 in both leaf and root tissues. There was no Cry34Ab1 leaf expression observed or detected in plant events transformed with the negative control construct, pDAB101556, that did not contain the cry34Ab1 gene. All constructs expressed the aad-1 gene in both root and leaf tissues.

Furthermore, the modified Zea mays chlorophyll a/b binding gene promoter regulatory element (SEQ ID NO: 3 and SEQ ID NO:4) drove the expression of Cry34Ab1 and AAD-1 protein expression in leaf (V4) as measured by ELISA in the $T_0$ transgenic plants (Table 3). The $T_0$ transgenic plants that were transformed with pDAB120165 represents expression of the modified Zea mays chlorophyll a/b binding gene promoter (SEQ ID NOs:3 and 4) in combination with St PinII 3'-UTR, while the $T_0$ transgenic plants transformed with pDAB120166 represents expression of the full length Zea mays chlorophyll a/b binding gene promoter (SEQ ID NOs:1 and 2) in combination with modified Zea mays chlorophyll a/b binding gene 3'-UTR (SEQ ID NO:8). These results indicate that the promoter (SEQ ID NOs:1-4) and 3'-UTR (SEQ ID NOs:7-8) sequences of this disclosure are functional for driving expression of a transgene in a gene expression cassette within transgenic $T_0$ maize plant events.

TABLE 1

ELISA results showing cry34Ab1 and AAD-1 transgene expression in V4-V6 maize leaves of various construct events. STD is an abbreviation for standard deviation.

| Construct Name | No. of Events Analyzed | Mean Cry34 (ng/cm$^2$) | Cry34 STD | Mean AAD-1 (ng/cm$^2$) | AAD-1 STD |
|---|---|---|---|---|---|
| pDAB114438 | 24 | 134 | 123 | 165 | 106 |
| pDAB108746 | 18 | 129 | 79 | 173 | 96 |
| pDAB101556 | 2 | 0 | 0 | 198 | 129 |

TABLE 2

ELISA assay results showing cry34 and AAD-1 transgene expression in V4-6 maize roots of various construct events. STD is an abbreviation for standard deviation.

| Construct Name | No. of Events Analyzed | Mean Cry34 (ppm) | Cry34 STD | Mean AAD-1 (ppm) | AAD-1 STD |
|---|---|---|---|---|---|
| pDAB114438 | 6 | 5 | 8 | 1196 | 800 |
| pDAB108746 | 4 | 2672 | 2981 | 538 | 304 |
| pDAB101556 | 2 | 0 | 0 | 1204 | 798 |

TABLE 3

Cry34Ab1 protein expression in leaf (V4) as driven by the full length Zea mays chlorophyll a/b binding gene promoter and terminated by the Zea mays chlorophyll a/b binding gene 3'-UTR for pDAB120166, and for the modified Zea mays chlorophyll a/b binding gene 3'-UTR for pDAB120165 was measured by ELISA in the $T_0$ transgenic plants. Also included is the protein expression in leaf (V4) for AAD-1. STD is an abbreviation for standard deviation.

| Construct No. | No. of $T_0$ events analyzed | Mean Cry34Ab1 (ng/mg) | Cry34 STD | Mean AAD-1 (ng/mg) | AAD-1 STD |
|---|---|---|---|---|---|
| pDAB120165 | 34 | 477 | 184 | 277 | 299 |
| pDAB120166 | 17 | 412 | 153 | 283 | 232 |

Example 7

$T_1$ Transgenic Plant Expression

The Cry34 ELISA results of $T_1$ transgenic plant events indicated that the Zea mays chlorophyll a/b binding gene promoter regulatory element (SEQ ID NO:1) drove aboveground preferred expression, specifically in leaf, stem and husk tissues, of Cry34Ab1. This data was generated from $T_1$ events that were transformed with construct pDAB114438. Furthermore, negligible expression of Cry34Ab1 by the Zea mays chlorophyll a/b binding gene promoter regulatory element (SEQ ID NO:1 and SEQ ID NO:2) was observed in the root, kernel, and pollen tissues of these events (Table 4). Interestingly the expression of Cry34Ab1 in cob tissue exhibited a 10-fold lower expression than expression of Cry34Ab1 in the silk tissue of the analyzed events. There was no Cry34Ab1 leaf expression observed or detected in plants events transformed with the negative control construct, pDAB101556. This construct, pDAB101556, does not contain the cry34Ab1 transgene. All constructs expressed the aad-1 gene in both root and leaf tissues.

TABLE 4

Cry34Ab1 and AAD-1 protein expression in different tissue types as measured by ELISA in the T₁ transgenic plants.

| Construct No. | Tissue analyzed | Total events analyzed | Total samples analyzed | Mean Cry34Ab1 (ng/mg) | Cry34 STD | Mean AAD-1 (ng/mg) | AAD-1 STD |
|---|---|---|---|---|---|---|---|
| pDAB101556 | Leaf V4 | 1 | 13 | 1 | 0 | 497 | 161 |
| pDAB114438 | Leaf V4 | 3 | 43 | 1014 | 451 | 108 | 142 |
| pDAB114438 | Leaf V12 | 3 | 12 | 1686 | 705 | 289 | 124 |
| pDAB114438 | Leaf R3 | 3 | 9 | 2454 | 1288 | 645 | 163 |
| pDAB101556 | Root V4 | 1 | 3 | 4 | 3 | 2722 | 234 |
| pDAB114438 | Root V4 | 3 | 9 | 5 | 7 | 1509 | 370 |
| pDAB114438 | Cob | 2 | 10 | 265 | 223 | 3477 | 512 |
| pDAB114438 | Silk | 2 | 5 | 2828 | 1434 | 3701 | 605 |
| pDAB114438 | Kernel | 2 | 7 | 24 | 18 | 2463 | 250 |
| pDAB114438 | Stem | 2 | 5 | 5439 | 2906 | 6807 | 1730 |
| pDAB114438 | Husk | 2 | 10 | 4333 | 1974 | 1746 | 391 |
| pDAB114438 | Pollen | 2 | 4 | 72 | 13 | 1427 | 341 |

STD is an abbreviation for standard deviation.

T₁ Cry34Ab1 ELISA results of leaf (V4) showed similar expression range the pDAB120166 and pDAB114438 transgenic events containing the full length *Zea mays* chlorophyll a/b binding gene promoter (SEQ ID NOs:1 and 2) with different 3'-UTRs as regulatory elements for the cry34ab1 gene. The former construct, pDAB120166, contained a modified *Zea mays* chlorophyll a/b binding gene 3'-UTR (SEQ ID NO:8) derived from the same gene as the promoter while the latter construct, pDAB114438, contained a St PinII 3'-UTR. T₁ leaf (V4) Cry34Ab1 (Table 5). Further included in the T₁ Cry34Ab1 ELISA results of leaf (V4) tissue were pDAB120165 transgenic events that contained the modified length *Zea mays* chlorophyll a/b binding gene promoter (SEQ ID NOs:3 and 4) with the St PinII 3'-UTR as regulatory elements for the cry34ab1 gene. The ELISA results of pDAB120165 transgenic events displayed approximately 50%-60% less expression compared to either pDAB120166 or pDAB114438 that contain the full length *Zea mays* chlorophyll a/b binding gene promoter (SEQ ID NOs: 1 and 2). Construct pDAB120165 contained a modified promoter (SEQ ID NOs:3 and 4) and PinII 3'-UTR. These results indicate that the promoter (SEQ ID NOs:1-4) and 3'-UTR (SEQ ID NOs:7-8) sequences of this disclosure are functional for driving expression of a transgene in a gene expression cassette within transgenic T₁ maize plant events.

TABLE 5

Cry34Ab1 and AAD-1 protein expression in Leaf (V4) as measured by ELISA in the T₁ transgenic plants of different constructs.

| Construct No. | Events analyzed | Samples analyzed | Cry34Ab1 (ng/mg) Mean | STD | AAD-1 (ng/mg) Mean | STD |
|---|---|---|---|---|---|---|
| Non-transgenic control | NA | 3 | 0 | NA | 0 | NA |
| pDAB120166 | 5 | 43 | 738 | 103 | 94 | 49 |
| pDAB114438 | 3 | 30 | 896 | 439 | 65 | 53 |
| pDAB120165 | 5 | 32 | 464 | 75 | 99 | 69 |

STD is an abbreviation for standard deviation.
NA = Not Applicable

As such, novel *Zea mays* chlorophyll a/b binding gene regulatory elements were identified and characterized which include: the full length *Zea mays* chlorophyll a/b binding gene promoters of SEQ ID NO:1, and SEQ ID NO:2; the modified *Zea mays* chlorophyll a/b binding gene promoters of SEQ ID NO:3, and SEQ ID NO:4; the *Zea mays* chlorophyll a/b binding gene intron of SEQ ID NO:5; the *Zea mays* chlorophyll a/b binding gene 5'-UTR of SEQ ID NO:19; the *Zea mays* chlorophyll a/b binding gene 5'-UTR of SEQ ID NO:19; the full length *Zea mays* chlorophyll a/b binding gene 3'-UTR of SEQ ID NO:7; and the modified *Zea mays* chlorophyll a/b binding gene 3'-UTR of SEQ ID NO:8. Disclosed for the first time are novel promoter regulatory elements for use in gene expression constructs.

What is claimed is:

1. A gene expression cassette comprising a promoter operably linked to a heterologous nucleic acid, wherein the promoter comprises a polynucleotide comprising a sequence identity of at least 90% to SEQ ID NO:2.

2. The gene expression cassette of claim 1, wherein the polynucleotide has at least 95% sequence identity to SEQ ID NO:2.

3. The gene expression cassette of claim 1, wherein the polynucleotide comprises an intron.

4. The gene expression cassette of claim 3, wherein the intron has at least 90% sequence identity to SEQ ID NO:5.

5. the gene expression cassette of claim 1, wherein the polynucleotide has at least 90% sequence identity to SEQ D NO: 1.

6. The gene expression cassette of claim 1, wherein the operably linked nucleic acid encodes a polypeptide or a small RNA.

7. The gene expression cassette of claim 1, wherein the nucleic acid is selected from the group consisting of a nucleic acid conferring insecticidal resistance, a nucleic acid conferring herbicide tolerance, a nucleic acid conferring nitrogen use efficiency, a nucleic acid conferring water use efficiency, a nucleic acid conferring nutritional quality, a nucleic acid encoding a DNA binding protein, and a nucleic acid encoding a selectable marker.

8. The gene expression cassette of claim 1 further comprising a 3'-untranslated region.

9. The gene expression cassette of claim 8, wherein the 3'-untranslated region has at least 90% sequence identity to SEQ ID NO:7 or SEQ ID NO;8.

10. The gene expression cassette of claim 1 further comprising a 5'-untranslated regions, wherein the 5'-UTR has at least 90% sequence identity to SEQ ID NO:19.

11. A recombinant vector comprising the gene expression cassette of claim 1, wherein the vector is selected from the group consisting of a plasmid, a cosmid, a bacterial artificial chromosome, a virus, and a bacteriophage.

12. A transgenic cell comprising the gene expression cassette of claim 1.

13. The transgenic cell of claim 12, wherein the transgenic cell is a transgenic plant cell.

14. A transgenic plant comprising the transgenic plant cell of claim 13.

15. The transgenic plant of claim 14, wherein the transgenic plant is a monocotyledonous plant or dicotyledonous plant.

16. The transgenic plant of claim 15, wherein the monocotyledonous plant is selected from the group consisting of a maize plant, a rice plant, and a wheat plant.

17. A transgenic seed from the transgenic plant of claim 14, wherein the seed comprises the gene expression cassette.

18. The gene expression cassette of claim 1, wherein the promoter is a tissue-preffered promoter.

19. The gene expression cassette of claim 1, wherein the tissue-preferred promoter is a leaf, husk, stem or silk tissue-preferred promoter.

20. The gene expression cassette of claim 1, wherein the promoter comprises the polynucleotide sequence of nucleotides 1-1,887 of SEQ ID NO: 2.

21. A method for expressing a coding sequence in a transgenic plant, the method comprising:
 a) transforming a plant cell with a gene expression cassette comprising a polynucleotide sequence comprising a sequence identity of at least 90% to SEQ ID NO:2 operably linked to a heterologous coding sequence, which is operably linked to a 3'-untranslated region;
 b) isolating the transformed plant cell comprising the gene expression cassette;
 c) regenerating a transgenic plant from the transformed plant cell; and,
 d) obtaining the transgenic plant, wherein the transgenic plant expresses the coding sequence.

22. A method for manufacturing a synthetic polynucleotide sequence comprising a sequence identity of at least 90% to SEQ ID NO:2, the method comprising:
 a) isolating a nucleic acid comprising a polynucleotide sequence comprising SEQ ID NO:2;
 b) producing a plurality of oligonucleotide primer sequences, wherein the oligonucleotide primer sequences bind to the nucleic acid under stringent hybridization conditions;
 c) ligating the plurality of oligonucleotide primer sequences to synthesize a synthetic polynucleotide sequence; and,
 d) sequencing the resulting synthetic polynucleotide to confirm that it comprises at least 90% identity to SEQ ID NO:2.

* * * * *

SEQUENCE LISTING

```
<160> NUMBER OF SEQ ID NOS: 19

<210> SEQ ID NO 1
<211> LENGTH: 2006
<212> TYPE: DNA
<213> ORGANISM: artificial sequence
<220> FEATURE:
<223> OTHER INFORMATION: Zea mays chlorophyll a/b binding gene promoter

<400> SEQUENCE: 1
gcacaaaata cataaaacta gattagaaaa ggaagagaat acgccaaatt gcagcttaat      60
caattagacg atttagtcct gtttttacga aacaattgtt taagataaca ttaggacatg     120
```

```
tacaatatgt gtctttggat gtgtttaagg agtaaatgta aaaaaaatag atacgtctct      180
taacgaagtc attgtgtctt ggctctatgc tcgagacgga gaaatagcta attgattaat      240
ttaatttatt gaatgttctt attggtgtaa tgaatatagt aaggcactgg ccttatactt      300
ggagtttggc atgtcttatg ctatgttgca acaggcccg gtcttgacat ttcgggggcc       360
ctaagagaaa atttatatag aggtcctata cgaaaatttg agtctgttat tttttcaact      420
tttaaataat atatgaaaaa taaaaaattg atgatttaca taattttatt caaaatgata      480
tgactggaaa tattgttaca gtattttatg agtcgtaaaa ttatataaat tatgtaatat      540
acatttgttt tgactttga gagagtattt ttacttttaa tttgtcaaac tagcctaaac       600
cttaaaatac acagtaaacc aaatctaaat acattagatc aaattttctg aaaataaagt      660
tcagcaaact aaactaggat taatcaatgt aggttattag ggtcgaccct tcggtaggct      720
agaattaagc aacgcgatag gcacaggtgt acaacaccct tcgtccttcc cacgtcaatt      780
ttagggcctg tttggttcac ggctaattat gccacacttt gcctaaggtt agtcgtccga      840
attgaagaac taaccttatg cagaaaagtt aggcaaagta tggcaagtta ggtagtaaac      900
caaacaggcc aaagtatttg tcatcaagca gacggttgcg cgacctcaaa gagatgattg      960
ctagaaaata aagagacgca acaaaagaat gaaaatatag atttatctat aacttatatg     1020
catttgatat aagatagata aatgggagcc ctacgaacct tgaggctctg agcagtcgca     1080
tatcctgcac acccttggcg ccggccctgg ttgcaaatat gcaattgtgt ccttatccgc     1140
gactggtcac gaggctagga ttgatcgaaa gctgccgatg agaaatggca agggcggcat     1200
gctgtggcct ttttttacg gtctgtcagg acaactgaaa agttacaaat ttatagtggt      1260
tgtaaacagc aacacgttaa aaagtcgatt atcagtttca cagaaagagg tcgttaaaac     1320
cgccagcaag cttgtttcac tatcagtctg tcgctaagac aatctctttc accaaaaata     1380
caatttgctt tcttgccgtt gcttcaagtg aaaatcttaa tgttttaaat taaaatatgt     1440
ggctctacgt aggaaaaaat aattcaatcg agtctcattt cataaaaaaa atttggtcaa     1500
aaaattatac accatctcgc tcaagtgact caaatatact aaacggtact gagctgtctt     1560
ataatataaa tttgatttac tgttagaata tgatgtttta tgagtgcact aaattctata     1620
aaatatattt atttttaaat tataagatat ttttataggt ctgctcttag agagagctaa     1680
aaaagagaga ggctgtctga agaaaaatcc ataaccaacg caaatcccg ggcgcccaat      1740 cagccttctc cgcggagatt cctagcctca gccagagcta cctcatctgc gtgaggctcc     1800
ggtggcgcca agtgttccgg catcccggac gcaccaatgg catccgagca acagatcttt     1860
tctgcaacaa cgcttcgcgt cgcggcggtg tttccctcca tctgctctgc tctttaaata     1920
cctccgtcgt ctcctcgtct ccacagcatc tcaagtcttc acactcctcg ccatcacata     1980
aaaccagtgc aagcagaagc agcgca                                          2006

<210> SEQ ID NO 2
<211> LENGTH: 1887
<212> TYPE: DNA
<213> ORGANISM: artificial sequence
<220> FEATURE:
<223> OTHER INFORMATION: Zea mays chlorophyll a/b binding gene
      upstream-promoter

<400> SEQUENCE: 2
gcacaaaata cataaaacta gattagaaaa ggaagagaat acgccaaatt gcagcttaat       60
caattagacg atttagtcct gttttacga aacaattgtt taagataaca ttaggacatg       120
```

```
tacaatatgt gtctttggat gtgtttaagg agtaaatgta aaaaaaatag atacgtctct    180
taacgaagtc attgtgtctt ggctctatgc tcgagacgga gaaatagcta attgattaat    240
ttaatttatt gaatgttctt attggtgtaa tgaatatagt aaggcactgg ccttatactt    300
ggagtttggc atgtcttatg ctatgttgca acaggcccg gtcttgacat ttcgggggcc     360
ctaagagaaa atttatatag aggtcctata cgaaaatttg agtctgttat ttttcaact     420 tttaaataat atatgaaaaa taaaaaattg atgatttaca taattttatt caaaatgata    480
tgactggaaa tattgttaca gtattttatg agtcgtaaaa ttatataaat tatgtaatat    540
acatttgttt tgacttttga gagagtattt ttacttttaa tttgtcaaac tagcctaaac    600
cttaaaatac acagtaaacc aaatctaaat acattagatc aaattttctg aaaataaagt    660
tcagcaaact aaactaggat taatcaatgt aggttattag ggtcgaccct tcggtaggct    720
agaattaagc aacgcgatag gcacaggtgt acaacacctt tcgtccttcc cacgtcaatt    780
ttagggcctg tttggttcac ggctaattat gccacacttt gcctaaggtt agtcgtccga    840
attgaagaac taaccttatg cagaaaagtt aggcaaagta tggcaagtta ggtagtaaac    900
caaacaggcc aaagtatttg tcatcaagca gacggttgcg cgacctcaaa gagatgattg    960
ctagaaaata aagagacgca acaaaagaat gaaaatatag atttatctat aacttatatg    1020
catttgatat aagatagata aatgggagcc ctacgaacct tgaggctctg agcagtcgca    1080
tatcctgcac acccttggcg ccggccctgg ttgcaaatat gcaattgtgt ccttatccgc    1140
gactggtcac gaggctagga ttgatcgaaa gctgccgatg agaaatggca agggcggcat    1200
gctgtggcct ttttttacg gtctgtcagg acaactgaaa agttacaaat ttatagtggt      1260
tgtaaacagc aacacgttaa aaagtcgatt atcagtttca cagaaagagg tcgttaaaac    1320
cgccagcaag cttgtttcac tatcagtctg tcgctaagac aatctctttc accaaaaata    1380
caatttgctt tcttgccgtt gcttcaagtg aaaatcttaa tgttttaaat taaaatatgt    1440
ggctctacgt aggaaaaaat aattcaatcg agtctcattt cataaaaaaa atttggtcaa    1500
aaaattatac accatctcgc tcaagtgact caaatatact aaacggtact gagctgtctt    1560
ataatataaa tttgatttac tgttagaata tgatgtttta tgagtgcact aaattctata    1620
aaatatattt attttaaat tataagatat ttttataggt ctgctcttag agagagctaa     1680
aaaagagaga ggctgtctga agaaaaatcc ataaccaacg caaatcccg ggcgcccaat     1740 cagccttctc cgcggagatt cctagcctca gccagagcta cctcatctgc gtgaggctcc    1800
ggtggcgcca agtgttccgg catcccggac gcaccaatgg catccgagca acagatcttt    1860
tctgcaacaa cgcttcgcgt cgcggcg                                        1887
```

<210> SEQ ID NO 3
<211> LENGTH: 1442
<212> TYPE: DNA
<213> ORGANISM: artificial sequence
<220> FEATURE:
<223> OTHER INFORMATION: modified Zea mays chlorophyll a/b binding gene
      promoter

<400> SEQUENCE: 3

```
gcacaaaata cataaaacta gattagaaaa ggaagagaat acgccaaatt gcagcttaat     60
caattagacg atttagtcct gttttttacga aacaattgtt taagataaca tggccttata   120
cttggagttt ggcatgtctt atgctatgtt gcaacaggc ccggtcttga catttcgggg     180
gccctaagag aaaatttata taggagtcct atacgaaaat ttgagtctgt tattttttca    240
```

```
acttttaaat aatatatgaa aaataaaaaa ttgatgattt acataatttt attcaaaatg    300
atatgactgg aaatattgtt acagtatttt atgagtcgta aaattatata aattatgtaa    360
tatacatttg ttttgacttt tgagagagta tttttacttt taatttgtca aactagccta    420
aaccttaaaa tacacagtaa accaaatcta aatacattag atcaaatttt ctgaaaataa    480
agttcagcaa actaaactag gattaatcaa tgtaggttat tagggtcgac ccttcggtag    540
gctagaatta agcaacgcga taggcacagg tgtacaacac ctttcgtcct tcccacgtca    600
ataaagtatt tgtcatcaag cagacggttg cgcgacctca aagagatgat tgctagaaaa    660
taaagagacg caacaaaaga atgaaaatat agatttatct ataacttata tgcatttgat    720
ataagataga taaatgggag ccctacgaac cttgaggctc tgagcagtcg catatcctgc    780
acacccttgg cgccggccct ggttgcaaat atgcaattgt gtccttatcc gcgactggtc    840
acgaggctag gattgatcga aagctgccga tgagaaatgg caagggcggc atgctgtggc    900 cttttttta cggtctgtca ggacaactga aaagttacaa atttatagtg gttgtaaaca    960
gcaacacgtt aaaagtcga ttatcagttt cacagaaaga ggtcgttaaa accgccagca   1020
agcttgtttc actatcagtc tgtcgctaag acaatctctt tcaccaaaaa tacaatttgc   1080
tttcttgccg ttgcttcaag tgaaaatctg agctaaaaaa gagagaggct gtctgaagaa   1140
aaatccataa ccaacgcaaa atcccgggcg cccaatcagc cttctccgcg gagattccta   1200
gcctcagcca gagctacctc atctgcgtga ggctccggtg gcgccaagtg ttccggcatc   1260
ccggacgcac caatggcatc cgagcaacag atcttttctg caacaacgct tcgcgtcgcg   1320
gcggtgtttc cctccatctg ctctgctctt taaatacctc cgtcgtctcc tcgtctccac   1380
agcatctcaa gtcttcacac tcctcgccat cacataaaac cagtgcaagc agaagcagcg   1440
ca                                                                  1442

<210> SEQ ID NO 4
<211> LENGTH: 1323
<212> TYPE: DNA
<213> ORGANISM: artificial sequence
<220> FEATURE:
<223> OTHER INFORMATION: modified Zea mays chlorophyll a/b binding gene
      upstream-promoter

<400> SEQUENCE: 4
gcacaaaata cataaaacta gattagaaaa ggaagagaat acgccaaatt gcagcttaat     60
caattagacg atttagtcct gttttacga aacaattgtt taagataaca tggccttata    120
cttggagttt ggcatgtctt atgctatgtt gcaacaggc ccggtcttga catttcgggg    180
gccctaagag aaaatttata tagaggtcct atacgaaaat ttgagtctgt tattttttca    240
acttttaaat aatatatgaa aaataaaaaa ttgatgattt acataatttt attcaaaatg    300
atatgactgg aaatattgtt acagtatttt atgagtcgta aaattatata aattatgtaa    360
tatacatttg ttttgacttt tgagagagta tttttacttt taatttgtca aactagccta    420
aaccttaaaa tacacagtaa accaaatcta aatacattag atcaaatttt ctgaaaataa    480
agttcagcaa actaaactag gattaatcaa tgtaggttat tagggtcgac ccttcggtag    540
gctagaatta agcaacgcga taggcacagg tgtacaacac ctttcgtcct tcccacgtca    600
ataaagtatt tgtcatcaag cagacggttg cgcgacctca aagagatgat tgctagaaaa    660
taaagagacg caacaaaaga atgaaaatat agatttatct ataacttata tgcatttgat    720
ataagataga taaatgggag ccctacgaac cttgaggctc tgagcagtcg catatcctgc    780
```

```
acacccttgg cgccggccct ggttgcaaat atgcaattgt gtccttatcc gcgactggtc    840
acgaggctag gattgatcga aagctgccga tgagaaatgg caagggcggc atgctgtggc    900 cttttttta cggtctgtca ggacaactga aaagttacaa atttatagtg gttgtaaaca     960
gcaacacgtt aaaagtcga ttatcagttt cacagaaaga ggtcgttaaa accgccagca    1020
agcttgtttc actatcagtc tgtcgctaag acaatctctt tcaccaaaaa tacaatttgc    1080
tttcttgccg ttgcttcaag tgaaaatctg agctaaaaaa gagagaggct gtctgaagaa    1140
aaatccataa ccaacgcaaa atcccgggcg cccaatcagc cttctccgcg gagattccta    1200
gcctcagcca gagctacctc atctgcgtga ggctccggtg cgccaagtg ttccggcatc     1260 ccggacgcac caatggcatc cgagcaacag atcttttctg caacaacgct tcgcgtcgcg    1320
gcg                                                                  1323
```

```
<210> SEQ ID NO 5
<211> LENGTH: 59
<212> TYPE: DNA
<213> ORGANISM: artificial sequence
<220> FEATURE:
<223> OTHER INFORMATION: Zea mays chlorophyll a/b binding gene intron
      (1)

<400> SEQUENCE: 5
gtgtttccct ccatctgctc tgctctttaa atacctccgt cgtctcctcg tctccacag    59
```

```
<210> SEQ ID NO 6
<211> LENGTH: 43
<212> TYPE: DNA
<213> ORGANISM: artificial sequence
<220> FEATURE:
<223> OTHER INFORMATION: Zea mays chlorophyll a/b binding gene intron
      (2)

<400> SEQUENCE: 6
gtggaggcgc caccgcccac cggccaccgc tgcggatatc tag                     43
```

```
<210> SEQ ID NO 7
<211> LENGTH: 1000
<212> TYPE: DNA
<213> ORGANISM: artificial sequence
<220> FEATURE:
<223> OTHER INFORMATION: Zea mays chlorophyll a/b binding gene 3'-UTR

<400> SEQUENCE: 7
gggggtggag cgccaccgc ccaccggcca ccgctgcgga tatctaggtg ttcggatgca     60
cgtgagcgcg cactggttcc agtttgtacc atgatgtaaa ttacttaccg taccagggtt    120
caatcggcaa ggaagaattg ttgtgttcac tgtcttgggc agtctcttgg tccaatatga    180
atcaacttac acagcatctc caaaaacttc taaaattact agctgaatgc ccgtgcgttg    240
caacgggaat atataatacc agtatactac gataacttat atacaaaatg tatgttatat    300
cgttatgaga aaatgtttca taaccaattt atgattctgg tcatacataa attttgttat    360
ttatagtcta tctgtttcac cactacattg caaccatcag tatcatgcag acttcgatat    420
atgttacgat ttgtatggtc tcattattgg agagcacgtt ccacacatac cggaagaaat    480
tttctcgtac atcgttagtc atcagacacg taccaccata cacttttgct taaacaaaaa    540
tgcaagtgtg tgtttgcgaa gagaattaaa ggcaagtcga cacaaaagct acccaacgg     600 tggcgaggat gacgaactgg tcattttttgt cggtcctccc ctgcgtcacc tctggcgcca    660
agatgacgcc atagtcctcg atatagtaat cgtcgaacgc gcgcgacata ccgagtactg    720
```

| | |
|---|---|
| atgactcttg gctgggctgt aaaacgaagt gcaccccggg ctcatcagca aggtagtacc | 780 |
| cctggtcgtt gcactaccgg atgcgctact actctacatg catcgtgttc gaggatactc | 840 |
| atacaacgtc agcaacggct atcgtctcag tgcacaagaa ttcatgccta gtcagtagcg | 900 |
| acttacgtgg ctggttgggc ttcaggtgaa cgatgagctg acaacgtgaa tggcgtcgtc | 960 |
| gtcgaatgca gtgcccagaa caacccgaaa gtcgccgacg | 1000 |

<210> SEQ ID NO 8
<211> LENGTH: 400
<212> TYPE: DNA
<213> ORGANISM: artificial sequence
<220> FEATURE:
<223> OTHER INFORMATION: modified Zea mays chlorophyll a/b binding gene 3'-UTR

<400> SEQUENCE: 8

| | |
|---|---|
| gggggtggag gcgccaccgc ccaccggcca ccgctgcgga tatctaggtg ttcggatgca | 60 |
| cgtgagcgcg cactggttcc agtttgtacc atgatgtaaa ttacttaccg taccaggttt | 120 |
| caatcggcaa ggaagaattg ttgtgttcac tgtcttgggc agtctcttgg tccaatatga | 180 |
| atcaacttac acagcatctc caaaaacttc taaaattact agctgaatgc ccgtgcgttg | 240 |
| caacgggaat atataatacc agtatactac gataacttat atacaaaatg tatgttatat | 300 |
| cgttatgaga aaatgtttca taccaatttt atgattctgg tcatacataa attttgttat | 360 |
| ttatagtcta tctgtttcac cactacattg caaccatcag | 400 |

<210> SEQ ID NO 9
<211> LENGTH: 3804
<212> TYPE: DNA
<213> ORGANISM: artificial sequence
<220> FEATURE:
<223> OTHER INFORMATION: Zea mays chlorophyll a/b binding gene sequence and regulatory elements

<400> SEQUENCE: 9

| | |
|---|---|
| gcacaaaata cataaaacta gattagaaaa ggaagagaat acgccaaatt gcagcttaat | 60 |
| caattagacg atttagtcct gttttttacga aacaattgtt taagataaca ttaggacatg | 120 |
| tacaatatgt gtctttggat gtgtttaagg agtaaatgta aaaaaaatag atacgtctct | 180 |
| taacgaagtc attgtgtctt ggctctatgc tcgagacgga gaaatagcta attgattaat | 240 |
| ttaatttatt gaatgttctt attggtgtaa tgaatatagt aaggcactgg ccttatactt | 300 |
| ggagtttggc atgtcttatg ctatgttgca aacaggcccg tcttgacat ttcgggggcc | 360 |
| ctaagagaaa atttatatag aggtcctata cgaaatttg agtctgttat ttttttcaact | 420 |
| tttaaataat atatgaaaaa taaaaaattg atgatttaca taatttttatt caaaatgata | 480 |
| tgactggaaa tattgttaca gtattttatg agtcgtaaaa ttatataaat tatgtaatat | 540 |
| acatttgttt tgacttttga gagtatttt ttacttttaa tttgtcaaac tagcctaaac | 600 |
| cttaaaatac acagtaaacc aaatctaaat acattagatc aaattttctg aaaataaagt | 660 |
| tcagcaaact aaactaggat taatcaatgt aggttattag ggtcgaccct tcggtaggct | 720 |
| agaattaagc aacgcgatag gcacaggtgt acaacacctt tcgtccttcc cacgtcaatt | 780 |
| ttagggcctg tttggttcac ggctaattat gccacacttt gcctaaggtt agtcgtccga | 840 |
| attgaagaac taaccttatg cagaaaagtt aggcaaagta tggcaagtta ggtagtaaac | 900 |
| caaacaggcc aaagtatttg tcatcaagca gacggttgcg cgacctcaaa gagatgattg | 960 |

```
ctagaaaata aagagacgca acaaaagaat gaaaatatag atttatctat aacttatatg    1020
catttgatat aagatagata aatgggagcc ctacgaacct tgaggctctg agcagtcgca    1080
tatcctgcac acccttggcg ccggccctgg ttgcaaatat gcaattgtgt ccttatccgc    1140
gactggtcac gaggctagga ttgatcgaaa gctgccgatg agaaatggca agggcggcat    1200
gctgtggcct ttttttacg gtctgtcagg acaactgaaa agttacaaat ttatagtggt     1260
tgtaaacagc aacacgttaa aaagtcgatt atcagtttca cagaaagagg tcgttaaaac    1320
cgccagcaag cttgtttcac tatcagtctg tcgctaagac aatctctttc accaaaaata    1380
caatttgctt tcttgccgtt gcttcaagtg aaaatcttaa tgttttaaat taaaatatgt    1440
ggctctacgt aggaaaaaat aattcaatcg agtctcattt cataaaaaaa atttggtcaa    1500
aaaattatac accatctcgc tcaagtgact caaatatact aaacggtact gagctgtctt    1560
ataatataaa tttgatttac tgttagaata tgatgtttta tgagtgcact aaattctata    1620
aaatatattt attttaaat taagatat ttttataggt ctgctcttag agagagctaa       1680 aaagagaga ggctgtctga agaaaaatcc ataaccaacg caaaatcccg ggcgcccaat     1740
cagccttctc cgcggagatt cctagcctca gccagagcta cctcatctgc gtgaggctcc    1800
ggtggcgcca agtgttccgg catcccggac gcaccaatgg catccgagca acagatcttt    1860
tctgcaacaa cgcttcgcgt cgcggcggtg tttccctcca tctgctctgc tctttaaata    1920
cctccgtcgt ctcctcgtct ccacagcatc tcaagtcttc acactcctcg ccatcacata    1980
aaaccagtgc aagcagaagc agcgcaatgg cgagcagcac catggccctc tcctccacag    2040
ccttcgccgg caaggcagtg aacgtgccgt cgtctctctt cggcgaggcc cgcgtgacga    2100
tgcgcaagac ggcggcgaag gcaaagccgg cggcgagctc cggcagcccg tggtacggcc    2160
ccgaccgcgt gctctacctg ggcccgctgt ccggcgcgcc cccgagctac ctgacgggcg    2220
agttcccggg cgactacggc tgggacaccg cggggctgtc ggcggacccg gagacgttcg    2280
ccaagaaccg ggagctggag gtcatccact cccgctgggc catgctgggc gcgttgggct    2340
gcgtgttccc ggagctgctc gcccgcaacg gcgtcaagtt cggcgaggcc gtgtggttca    2400
aggccgggtc gcagatcttc agcgagggtg ggctggacta cctcggcaac ccgagcctga    2460
tccacgcgca gagcatcctc gccatctggg cctgccaggt cgtgctcatg ggcgccatcg    2520
aggggtaccg cgtcgccggc ggccgctcg gagaggtcgt cgaccgctc taccccggcg       2580 gcagcttcga cccgctcggc ctcgccgacg accctgaggc cttgcggag ctcaaggtga     2640 aggagctcaa gaacgccgc ctcgccatgt tctccatgtt cgggttcttc gtccaggcca      2700
tcgtcaccgg caagggcccg ctcgagaacc tcgccgacca cctcgccgac cccgtcaaca    2760
acaacgcatg ggcctatgcc accaactttg tgcccggcaa gtgagggggt ggaggcgcca    2820
ccgcccaccg gccaccgctg cggatatcta ggtgttcgga tgcacgtgag cgcgcactgg    2880
ttccagtttg taccatgatg taaattactt accgtaccag ggttcaatcg gcaaggaaga    2940
attgttgtgt tcactgtctt gggcagtctc ttggtccaat atgaatcaac ttacacagca    3000
tctccaaaaa cttctaaaat tactagctga atgcccgtgc gttgcaacgg aatatataa     3060 taccagtata ctacgataac ttatatacaa aatgtatgtt atatcgttat gagaaaatgt    3120
ttcataacca atttatgatt ctggtcatac ataaattttg ttatttatag tctatctgtt    3180
tcaccactac attgcaacca tcagtatcat gcagacttcg atatatgtta cgatttgtat    3240
ggtctcatta ttgagagca cgttccacac ataccggaag aaattttctc gtacatcgtt      3300
agtcatcaga cacgtaccac catacacttt tgcttaaaca aaaatgcaag tgtgtgtttg    3360
```

```
cgaagagaat taaaggcaag tcgacacaaa agctacccca acggtggcga ggatgacgaa    3420
ctggtcattt ttgtcggtcc tcccctgcgt cacctctggc gccaagatga cgccatagtc    3480
ctcgatatag taatcgtcga acgcgcgcga cataccgagt actgatgact cttggctggg    3540
ctgtaaaacg aagtgcaccc cgggctcatc agcaaggtag tacccctggt cgttgcacta    3600
ccggatgcgc tactactcta catgcatcgt gttcgaggat actcatacaa cgtcagcaac    3660
ggctatcgtc tcagtgcaca agaattcatg cctagtcagt agcgacttac gtggctggtt    3720
gggcttcagg tgaacgatga gctggacaac gtgatggcgt cgtcgtcgaa tgcagtgccc    3780
agaacaaccc gaaagtcgcc gacg                                           3804

<210> SEQ ID NO 10
<211> LENGTH: 17
<212> TYPE: DNA
<213> ORGANISM: artificial sequence
<220> FEATURE:
<223> OTHER INFORMATION: primer

<400> SEQUENCE: 10
gccataccct ccagttg                                                    17

<210> SEQ ID NO 11
<211> LENGTH: 23
<212> TYPE: DNA
<213> ORGANISM: artificial sequence
<220> FEATURE:
<223> OTHER INFORMATION: primer

<400> SEQUENCE: 11
gccgttgatg gagtagtaga tgg                                             23

<210> SEQ ID NO 12
<211> LENGTH: 18
<212> TYPE: DNA
<213> ORGANISM: artificial sequence
<220> FEATURE:
<223> OTHER INFORMATION: primer

<400> SEQUENCE: 12
ccgaatccaa cggcttca                                                   18

<210> SEQ ID NO 13
<211> LENGTH: 18
<212> TYPE: DNA
<213> ORGANISM: artificial sequence
<220> FEATURE:
<223> OTHER INFORMATION: primer

<400> SEQUENCE: 13
tggcggacga cgacttgt                                                   18

<210> SEQ ID NO 14
<211> LENGTH: 19
<212> TYPE: DNA
<213> ORGANISM: artificial sequence
<220> FEATURE:
<223> OTHER INFORMATION: primer

<400> SEQUENCE: 14
aaagtttgga ggctgccgt                                                  19

<210> SEQ ID NO 15
```

```
<211> LENGTH: 21
<212> TYPE: DNA
<213> ORGANISM: artificial sequence
<220> FEATURE:
<223> OTHER INFORMATION: primer

<400> SEQUENCE: 15
cgagcagacc gccgtgtact t                                              21

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
tgttcggttc cctctaccaa                                                20

<210> SEQ ID NO 17
<211> LENGTH: 22
<212> TYPE: DNA
<213> ORGANISM: artificial sequence
<220> FEATURE:
<223> OTHER INFORMATION: primer

<400> SEQUENCE: 17
caacatccat caccttgact ga                                             22

<210> SEQ ID NO 18
<211> LENGTH: 24
<212> TYPE: DNA
<213> ORGANISM: artificial sequence
<220> FEATURE:
<223> OTHER INFORMATION: primer

<400> SEQUENCE: 18
cacagaaccg tcgcttcagc aaca                                           24

<210> SEQ ID NO 19
<211> LENGTH: 60
<212> TYPE: DNA
<213> ORGANISM: artificial sequence
<220> FEATURE:
<223> OTHER INFORMATION: Zea mays chlorophyll a/b binding gene 5'-UTR

<400> SEQUENCE: 19
catctcaagt cttcacactc ctcgccatca cataaaacca gtgcaagcag aagcagcgca    60
```